(12) United States Patent
Masakari et al.

(10) Patent No.: US 9,701,949 B2
(45) Date of Patent: Jul. 11, 2017

(54) AMADORIASE WITH IMPROVED THERMOSTABILITY, GENE AND RECOMBINANT DNA FOR THE AMADORIASE, AND METHOD FOR PRODUCTION OF AMADORIASE WITH IMPROVED THERMOSTABILITY

(71) Applicant: KIKKOMAN CORPORATION, Noda-shi, Chiba (JP)

(72) Inventors: Yosuke Masakari, Noda (JP); Atsushi Ichiyanagi, Noda (JP)

(73) Assignee: KIKKOMAN CORPORATION, Chita (JP)

(*) Notice: Subject to any disclaimer, the term of this patent is extended or adjusted under 35 U.S.C. 154(b) by 99 days.

(21) Appl. No.: 14/369,192

(22) PCT Filed: Dec. 27, 2012

(86) PCT No.: PCT/JP2012/083779
§ 371 (c)(1),
(2) Date: Jun. 27, 2014

(87) PCT Pub. No.: WO2013/100006
PCT Pub. Date: Jul. 4, 2013

(65) Prior Publication Data
US 2014/0356928 A1 Dec. 4, 2014

(30) Foreign Application Priority Data
Dec. 28, 2011 (JP) .................................. 2011-287651

(51) Int. Cl.
*C12N 9/06* (2006.01)
(52) U.S. Cl.
CPC .......... *C12N 9/0032* (2013.01); *C12Y 105/03* (2013.01)
(58) Field of Classification Search
None
See application file for complete search history.

(56) References Cited

U.S. PATENT DOCUMENTS

| | | | |
|---|---|---|---|
| 5,370,990 | A | 12/1994 | Staniford et al. |
| 6,033,867 | A | 3/2000 | Kato et al. |
| 7,018,823 | B2 | 3/2006 | Kurosawa et al. |
| 7,070,948 | B1 | 7/2006 | Sakaue et al. |
| 7,588,910 | B2 | 9/2009 | Matsuoka et al. |
| 7,951,553 | B2 | 5/2011 | Taniguchi et al. |
| 8,497,083 | B2 | 7/2013 | Ikebukuro et al. |
| 8,721,853 | B2 | 5/2014 | Ikebukuro et al. |
| 9,062,286 | B2 | 6/2015 | Ichiyanagi et al. |
| 2003/0157593 | A1 | 8/2003 | Kurosawa et al. |
| 2008/0113381 | A1 | 5/2008 | Matsuoka et al. |
| 2008/0233605 | A1 | 9/2008 | Taniguchi et al. |
| 2009/0239239 | A1 | 9/2009 | Hirokawa et al. |
| 2011/0136202 | A1 | 6/2011 | Hirokawa et al. |
| 2011/0195444 | A1 | 8/2011 | Hirao et al. |
| 2012/0003678 | A1 | 1/2012 | Aisaka et al. |
| 2012/0202235 | A1 | 8/2012 | Ikebukuro et al. |
| 2015/0247129 | A1 | 9/2015 | Ichiyanagi et al. |

FOREIGN PATENT DOCUMENTS

| | | |
|---|---|---|
| EP | 1 291 416 A1 | 3/2003 |
| EP | 1344828 A1 | 9/2003 |
| JP | 05-033997 B | 5/1993 |
| JP | 11-127895 A | 5/1999 |
| JP | 2001-095598 A | 4/2001 |
| JP | 2003235585 A | 8/2003 |
| JP | 2004-275013 A | 10/2004 |
| JP | 2004-275063 A | 10/2004 |
| JP | 4231668 B2 | 3/2009 |
| JP | 2010-035469 A | 2/2010 |
| JP | 2010-057474 A | 3/2010 |
| JP | 2010-115189 A | 5/2010 |
| JP | 2010104278 A | 5/2010 |
| JP | 2010148358 A | 7/2010 |
| JP | 2010233501 A | 10/2010 |
| JP | 2010233502 A | 10/2010 |
| JP | 2011-229526 A | 11/2011 |
| WO | WO 97/13872 A1 | 4/1997 |
| WO | WO 2004/104203 A1 | 12/2004 |
| WO | WO 2005/049857 A1 | 6/2005 |
| WO | WO 2007/125779 A1 | 11/2007 |
| WO | WO 2010/041419 A1 | 4/2010 |
| WO | WO 2010/041715 A1 | 4/2010 |
| WO | 2011015326 A2 | 2/2011 |
| WO | WO 2011/015325 A1 | 2/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Extended European Search Report dated Oct. 8, 2015, issued in counterpart European Application No. 12863477.1.
International Search Report for PCT/JP2012/083779 mailed on Feb. 19, 2013.
Kozo Hirokawa et al., "Enhancement of thermostability of fungal deglycating enzymes by directed evolution", *Appl. Microbiol. Biotechnol.*, 78, 775-781, (2008).
Ryuichi Sakaue et al., "Thermostability of Bacterial Fructosyl-Amino Acid Oxidase by Directed Evolution", *Applied & Environ. Microbiol.*, 69(1), 139-145 (2003).
Kozo Hirokawa et al., "Molecular cloning and expression of novel fructosyl peptide oxidases and their application for the measurement of glycated protein," *Biochem. Biophys. Res. Commun.*, 311, 104-111, (2003).

(Continued)

*Primary Examiner* — Christian Fronda
(74) *Attorney, Agent, or Firm* — Holtz, Holtz & Volek PC

(57) ABSTRACT

An amadoriase having a substitution or a deletion of one or more amino acid residues at positions corresponding to amino acids selected from the group consisting of three amino acid residues from the carboxyl terminal and amino acids at positions 151, 43, 53, 267, 350, 185, 196, 299 and 323 in the amino acid sequence of amadoriase derived from the *Coniochaeta* species indicated in SEQ ID NO: 1. The amadoriase having a heat resistance which is superior to that of a conventional amadoriase.

9 Claims, 1 Drawing Sheet

(56) References Cited

OTHER PUBLICATIONS

Seungsu Kim et al., "Motif-Based Search for a Novel Fructosyl Peptide Oxidase From Genome Databases,", *Biotechnol. Bioeng.*, 106, 358-366, (2010).
Maki Fujiwara et al., "Alteration of Substrate Specificity of Fructosyl-Amino Acid Oxidase from *Ulocladium* sp. JS-103," *J. Biosci. Bioeng.*, 102, 241-243, (2006).
Nobuyuki Yoshida et al., "Primary structures of fungal fructosyl amino acid oxidases and their application to the measurement of glycated proteins," *Eur. J. Biochem.*, 242, 499-505, (1996).
Hyo-Young, Jeong et al., "The *veA* gene is necessary for the inducible expression by fructosyl amines of the *Aspergillus nidulans faoA* gene encoding fructosyl amino acid oxidase (amadoriase, EC 1.5.3)," *Arch. Microbiol.*, 178, 344-350, (2002).
Stefano Ferri et al., "Cloning and Expression of Fructosyl-amine Oxidase from Marine Yeast *Pichia* Species N1-1," *Mar. Biotechnol.*, 6, 625-632, (2004).
Yasuyoshi Sakai et al., "Purification and Properties of Fructosyl Lysine Oxidase from *Fusarium oxysporum* S-1F4," *Biosci. Biotech. Biochem.*, 59(3), 487-491, (1995).
Maki Fujiwara et al., "Alteration of substrate specificity of fructosyl-amino acid oxidase from *Fusarium oxysporum,*" *Appl. Microbiol. Biotechnol.*, 74:813-819, (2007).
Ryoichi Sakaue et al., "Cloning and Expression of Fructosyl-amino Acid Oxidase Gene from *Corynebacterium* sp. 2-4-1 in *Escherichia coli,*" *Biosci. Biotechnol. Biochem.*, 66(6), 1256-1261, (2002).
Kozo Hirokawa et al., Recombinant *Agrobacterium* AgaE-like Protein with Fructosyl Amino Acid Oxidase Activity, *Biosci. Biotechnol. Biochem.*, 66(11), 2323-2329, (2002).
Stefano Ferri et al., "Isolation and characterization of a fructosyl-amine oxidase from an *Arthrobacter* sp.," *Biotechnology Letters*, 27: 27-32, (2005).
International Preliminary Report on Patentability (IPRP) including Written Opinion dated Jul. 10, 2014 in parent International Application No. PCT/JP2012/083779.
U.S. Appl. No. 13/814,692; First Named Inventor: Atsushi Ichiyanagi; Title: "Amadoriase Having Altered Substrate Specificity"; filed Feb. 6, 2013.
U.S. Appl. No. 14/715,739; First Named Inventor: Atsushi Ichiyanagi; Title: "Amadoriase Having Altered Substrate Specificity"; filed May 19, 2015.
Gen Bank Accession No. BAD00186.1, published Oct. 31, 2003.
Gen Bank Accession No. BAE93140.1, published Apr. 5, 2006.
Gen Bank Accession No. XP 002477846.1, available May 2, 2007.
Gen Bank Accession No. XP001798711.1, published Apr. 2, 2008.
Gen Bank Accession No. XP001938761.1, published May 30, 2008.
Gen Bank Accession No. XP002559397.1, published Aug. 14, 2009.
Gen Bank Accession No. XP456462.1, published Apr. 15, 2010.
Gen Bank Accession No. XP569819.1, published Apr. 24, 2006.
Gen Bank Accession No. XP777019.1, published Mar. 21, 2008.
Gen Bank Accession No. AAF28476.1, published Jan. 30, 2000.
Gen Bank Accession No. BAD00185.1, published Oct. 31, 2003.
Delpierre, et al., "Identification of Fructosamine Residues Deglycated by Fructosamine-3-kinase in Human Hemoglobin", The Journal of Biological Chemistry, vol. 279, No. 26, Issue of Jun. 25, pp. 27613-27620, 2004.
Ferri, et al., "Review of Fructosyl Amino Acid Oxidase Engineering Research: A Glimpse into the Future of Hemoglobin A1c Biosensing", Journal of Diabetes Science and Technology, May 2009, 3(3):585-592.
Guo, et al., "Protein tolerance to random amino acid change", Proceedings of the National Academy of Sciences USA, vol. 101, No. 25, pp. 9205-9210, 2004.
Lin, et al., "Occurrence, characteristics, and applications of fructosyl amine oxidases (amadoriases)", Applied Microbiology and Biotechnology, vol. 86, pp. 1613-1619, 2010.
Miura, et al., "Development of fructosyl amine oxidase specific to fructosyl valine by site-directed mutagenesis", Protein Engineering, Design & Selection vol. 21 No. 4 pp. 233-239, 2008 Published online Jan. 31, 2008.

* cited by examiner

```
                                                          ●43位      ●53位
Co    1 MTSNRADTRVIVVGGGGTIGSSTALHLVRSGYAPASITVLDTFEIPSAQSAGHDLNKIMGIRLRNKVDLQMSLEARQMWKEDELFQPFFHNTGRMDCEHT 100
Et    1 MAHSRASTKVVVVGGGGTIGSSTALHLIRSGYTPSNITVLDVYKTPSLQSAGHDLNKIMGIRLRNGPDLQLSLESLDMWQNDELFKPFFHQVGMIDCSSS 100
Py    1 MAASRAKTTVIVVGGGGTIGSSTALHLLRSGYTPSNITVLDTYPIPSLGSAGHDLNKIMGIRLRNKVDLQLSLEARENWREDELFRDFFHNTGRLDCAHG 100
Ar    1 MAASRNTTKVIVVGGGGTIGSSTALHLLRSGYTATNITVLDTYPIPSAQSAGHDLNKIMGIRLRNPVDKQLSLEAQDMWCHDELFKPYFHNTGRMDCEGT 100
Cc    1 MAPSRANTSVIVVGGGGTIGSSTALHLVRSGYTPSNITVLDTYPIPSAQSAGHDLNKIMGIRLRNKVDLQLSLEARQMWREDDLFKEYFHNTGRLDCAHG 100
Nv    1 MTTPRKETTVLIIGGGGTIGSSTALHLLRAGYTPSNITVLDTYPIPSAQSAGHDLNKIMGIRLRNKVDLQLSLEARDMWRNDALFRPFFHNTGRLDCESS 100
Cn    1 MPPSRASTKVIIGGGGTLGSSTALHLLRAGYTPSNITVLDTYLIPSAQSAGHDLNKIMGIRIRNPVDKQLSLEARDMWRNDEVFKPYFHNTGRLDCAHT 100
Pn    1 MAPSRANTSVIVVGGGGTIGSSTALHLVRSGYTPSSQSAGHDLNKIMGVSLRNPVDLQLALEARQMWRNDELFKKFFHNTGRLDCAHG 100
An    1 -MTPRANTKIIVVGGGGTMGSSTALHLLRAGYTPSNITVLDTCPIPSAQSAGYDLNKIMSIRLRNKPDLQLSLEALDMWKNDPLFKPFFHNVGMIDVSST 99
Ul    1 MAPNRANISVIVVGGGGTIGSSTALHLVRSGYTPSNITVLDTYPIPSAQSAGHDLNKIMGIRLRNKVDLQLSLEARQMWTEDDLFKEYFHKTGRLDCAHG 100
Pc    1 MAHSRESTKIVIVGGGGTMGSSTALHLIRSGYTPSNITVLDVYPIPSLQSAGYDLNKIMSIRLRNGPDWQLSLEALDMWKNDPLFKPFFHNVGMLDCSSS 100
          *   :::;****;********;*;**;..;*;****.    **   ***  ******.;  ;** * *;:**; ;** .* :*; :**;.* :*

●151位                      ●185位       ●196位
Co  101 PEGIEDLKKQYQALMDAGAGLEKTHAWLDNEDEILSKMPLLQRDQIQGWKAIWSQDGGWLAAAKAINAIGQFLKERGVKFGFGDAGSFKQPLFDDEG-TT 199
Et  101 KEGIENLRRKYQTLLDAGIGLEKTNVWLESEDEILAKAPNFTREQVKGWKGLFCTDGGWLAAAKAINAIGIPLQDKGVKFGFGDAGTFQQPLFAADG-KT 199
Py  101 EKGINDLRQAYQTLLDANAGLEETNEWLDSEDEILARMPLLSREQVKGWKAVFSRDGGWLAAGKAINAIGEYLRKEGVKFGFGGAGSFQQPLLAEG---I 197
Ar  101 EKGIAALKQQYQTLLDADVGLEKTTEWLDSEDAILAKMPLLERDQIKGWKAIFSQDGGWLAAAKAINAIGEHLKRQGVNFGFGGAGAFEKPLFAPDG-ST 199
Cc  101 EEGLADLRQAYQALLDANAGLEETTEWLDSEDEILKKMPLLDREQIKGWKAVYSQDGGWLAAAKAINAIGEYLRAQGVKFGFGCAGSFKQPLLAEG---V 197
Nv  101 AEGVEGLRREYQRLVEAGVGLEETHEWLDSEEAILEKAPLLQREEIEGWKAIWSEEGGWLAAAKAINAIGEELQRQGVRFGFGGAGSFKPLFADDG-TT 199
Cn  101 PESIASLRKSYEAILKAGSGLEKTHHWLSTEDEILARAPLLDRKQIKGWKAIYSEDGGWLAAAKAINSIGQVLKEKGVTFGFGSAGSFKKPLFDEDG-TK 199
Pn  101 EKDIADLKSGYQALVDA--GLDATNEWLDSEDEILKRMPLLSRDQIKGWKAIFSKDGGWLAAAKAINAVGEYLRDQGVRFPGFYGAGSFKAPLLAEG---V 195
An  100 EEGIEGLRRKYQSLLDAGIGLEKTNFMLESKDEILAKAPHFTQEQIKGWKGLFCGDGGWLAAAKAINAIGQFLKKQGVKFGFGAGTFKKPLFADAHEKT 199
Ul  101 EKGLADLKQAYQALLDANAGLEATTEWLDSEDKILERMPLLNRDQIKGWKAVFSEDGGWLAAAKAINAIGRFLRDQGVKFGFGGAGSFKQPLLAEG---V 197
Pc  101 QEGIASLRRKHQDLIDANIGLEKTNIWLESEDDILAKAPHFAREQIKGWKGLFCGDGGWLAAAKAINAIGTFLKSQGVKFGFGSAGTFKRPLFAPDG-AT 199
          :.: *: :: : .* **; *  *..*; **; * *  * .;.*;.11***.::. :*****.****;;* *;.** *** .**;*; **;

●267位
Co  200 CIGVETADGTKYYADKVVLAAGANSPTLVDLEDQCCSKAWVYARIQLTPEEAAEYKGVPVVYNGELGFFFKPDEFGVIKVCDEFPGFS-RFKEHQPYGAP 298
Et  200 CIGLETTDGTKYFADKVVLAAGANSPTLVDLEDQCVSKAWVFAHIQLTPKEADAYKNVPVVYDGEYGFFFEPDEYGVIKVCDEFPGFS-RFKLHQPYGAA 298
Py  198 CIGVETTDGTRYYADKVVLAAGANSPALVDLEDQCVSKAWVYAHMQLTPKEAAAYKDTPVVYNGDLGFFFEPMEHGVIKVCDEFPGFT-RFKKHQPPGAR 296
Ar  200 CIGVETVDGTKYYGDKVVLAAGANSPVLVDLEEQCCSKAWVYAHMQLTPHEAAEYQGCPVVYHGDLGFFFEPNEHGVIKVCDEFPGFTRFLEQHQSYGAP 299
Cc  198 CIGVETVDGTQYYADKVVLAAGANSPVLVDLEDQCCSKAWVYARIQLTPEEAAEYKNVPVVYNGDVGFFFEPDEHGVIKVCDEFPGFT-RFKQHQPYEAK 296
Nv  200 CIGVETVDGTQYFADKVVLAAGANSPALVDLEEQCCSKAWVYAHMQLTPEEAAVYKGCPVVYHGDVGFFFEPMEHGVIKVCDEFPGFT-RFKQHQPYGAP 298
Cn  200 AIGIETVDGTQYFADKVVLAAGANSPTLVDLEGQCCSKAWYAHMQLTPEEAAEYKECPVVYNSELGFFFEPREHGVIKVCDEFPGFT-RFKQHQPYGAS 298
Pn  196 CIGVETVDGTRYYADKVVLAAGANSPTLVELHEQCVSKAWVYGHIQLTPEEAARYKNSPVVYNGDVGFFFKPNEHGVIKVCDEFPGFT-RFKMHQPFGAK 294
An  200 CIGVETVDGTKYYADKVVLAAGANSSTLVDLEEQCVSKAWVFAHIQLTPAEAAAYKNTPVIYDGDYGFFFEPMENGIIKVCDEFPGFT-HFKMHQPYGSP 298
Ul  198 CVGVETVDGTRYYADKVVLAAGANSPALVDLQDQCVSKAWVYAHIQLTPEEAAEYKNVPVVYNGDVGFFFEPDEYGVIKVCDEFPGFT-RFKQHQPYGAS 296
Pc  200 CSGVETVDGTKYFADKVVLAAGANSSTLVDLEDQCVSKAWVFAHIQLTPQKSAQYKDVPVVYDGDYGFFFEPMEHGVIKVCDEFPGFS-RFKLHQPGAT 298
          . *:**.***:*.,**********.,..**;*. **.*****;,*;**;** *;. *; **.:*..; *****;* *;*********. :: **.:*;

●299位     ●323位    ●350位
Co  299 SPKRISVPRSHAKHPTDTYPDASEVSIKKAIATFLPRFQDKELFNRALGWKCTDTADAALLMCENPEWKNFILATGDSGHSFKILPNVGKYVVELIEGRLP 398
Et  299 SPKMISVPRSNAKHPTDTYPDASEVTIRKAIRPLPSFKDKELFNRTMCWGTDTADANLLICENPKWKNPILATGDSGHSFKLLPNIGKYVVELLEGSLS 398
Py  297 APKRISVPRSNAKHPTDTYPHASEASIKKAIAAFLPQFKDKELFHRCHCTDTADAALLICENPRWRNFILATGDSGHSFKLLPNIGKHVVELLEGTLA 396
Ar  300 APTRVSVPRSNAKHPTDTYPDASEQSIRRAVAAFLPRFQSKELFNRAMCWCTDTADAALLICENPMRWNFILATGDSGHSFKLLPNIGKHVVELLEGRLA 399
Cc  297 APKRISVPRSAAKHPTDTYPDASEKSIRKKAIATFLPKFTEKELFNRHLGWCTDTADAALLMCENPEWKNFVLATGDSGHTFKLLPNIGKHVVELLEGTLA 396
Nv  299 APKPVSVPRSNAKHPTDTYPDASEESIKRAVSTFLPRFDKPLFNRADTADSALLICEMPRWKNFLLPIIGKHVVELVEGRLA 398
Cn  299 STKHISFPRSNAKHPTDTIPDESDASIRRAISAPLPRFKEKELFNRALCWCTDTADANLLICEHPRWKNFILATGDSGHSFKILPNIGKHVVELIEGTLA 398
Pn  295 APKRISVPRSNAKHPTDTIPDASDVSIRRAIATFMPQFKNKRMPNQAMKCNCTDTADAALLICENPENWKFYLATGDSGHSFKLLPNIGKHVVELLEGTLA 394
An  299 APKRISVPRSNAKHPTDTYPHASEVTIRKKAIKRPLPRFNDKELFNRAMCWCTDTADANLLVCENPRWKGFYLATGDSGHSFKLLPNIGKHVVELEERLE 398
Ul  297 APKRISVPRSAAKHPTDTYPDASEVSIRKAIATFLPKFTEKEVFNRHLCWCTDTADAALLMCENPKWKWFVLATGDSGHTFKLLPNIGKHVVELLEGTLA 396
Pc  299 SPKLISVPRSNAKHPTDTYPDSSEETIRKAIARFMPRFKDKELFNRSMCWCTDTADABLLICENPKWNWFILATGDSGHSFKVLPNIGKHVVELIEGRLP 398
          :.. ;*.*** ******* *, *:;;*;  *:*.* .* :** ;******** *;.* *******: **.***.*;. * ********;** :*;****;* *

Co  399 EEMAYQWRWRPG-GDALKSRRAAPPKDLADMPGWKHDPKL---------------------------------------- 437
Et  399 QEMAGAWRWRPG-GDALRSRRGAPAKDLAEMPGWKHDAHL---------------------------------------- 437
Py  397 ADLAHAWRWRPGIGDALQSRRAAPAKDLADMPGWMHDESPRAKL------------------------------------ 440
Ar  400 DDLAQAWRWRPGQGDALKSRRAAPAKDLADMPGWMHDGDSGHATSGTSSEHKL---------------------------- 452
Cc  397 EDLAHAWRWRPGTGDALKSRRAAPAKDLADMPGWKHDDVVKSKL------------------------------------ 440
Nv  399 DDLAEAWRWRPGQGDARKSIRAAPAKDLADMPGWKHDQDSESR-------------------------------------- 441
Cn  399 EDLAESWRWRPGSGDPLISRRAAPAKDLADLPGWNHDEPSDDDMDVKDVAVSLASVKIGESIGEKVVEDGARVGVKVLA 477
Pn  395 DDLAHAWRWRPGSGDALKSRRSAPAKDLADMPGWMHDKPRAML------------------------------------- 437
An  399 SVPKDAWRWRPGSGDALKSRRAAPAKDLADMPGWRMEAKM---------------------------------------- 438
Ul  397 DDLAHAWRWRPGTGDALKSRRARAKDLADMPGWMHDGEAPRAEL------------------------------------ 441
Pc  399 QDLAGAWRWRPG-GDALKSKRSAPAKDLAEMPGWKHDAKL---------------------------------------- 437
          ; ****** **. * *.* .;***;****.;;
```

Co: Coniochaeta species-derived amadoriase
Et: Eupenicillium terrenum-derived amadoriase
Py: Pyrenochaeta species-derived ketoamine oxidase
Ar: Arthrinium species-derived ketoamine oxidase
Cc: Curvularia clavata-derived ketoamine oxidase
Nv: Neocosmospora vasinfecta-derived ketoamine oxidase
Cn: Cryptococcus neoformans-derived fructosyl amino acid oxidase
Pn: Phaeosphaeria nodorum-derived fructosyl peptide oxidase
An: Aspergillus nidulans-derived fructosyl amino acid oxidase
Ul: Ulocladium species-derived fructosyl amino acid oxidase
Pc: Penicillium crysogenum-derived fructosyl amino acid oxidase

SEQUENCE LISTING

<160> NUMBER OF SEQ ID NOS: 33

<210> SEQ ID NO 1
<211> LENGTH: 437
<212> TYPE: PRT
<213> ORGANISM: Coniochaeta sp.

<400> SEQUENCE: 1

-continued

```
Met Thr Ser Asn Arg Ala Asp Thr Arg Val Ile Val Gly Gly Gly
 1               5                  10                 15

Gly Thr Ile Gly Ser Ser Thr Ala Leu His Leu Val Arg Ser Gly Tyr
             20                  25                  30

Ala Pro Ala Asn Ile Thr Val Leu Asp Thr Phe Glu Ile Pro Ser Ala
             35                  40                  45

Gln Ser Ala Gly His Asp Leu Asn Lys Ile Met Gly Ile Arg Leu Arg
 50                  55                  60

Asn Lys Val Asp Leu Gln Met Ser Leu Glu Ala Arg Gln Met Trp Lys
 65                  70                  75                  80

Glu Asp Glu Leu Phe Gln Pro Phe Phe His Asn Thr Gly Arg Met Asp
                 85                  90                  95

Cys Glu His Thr Pro Glu Gly Ile Glu Asp Leu Lys Lys Gln Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Asp Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Leu Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
```

His Asp Pro Lys Leu
    435

<210> SEQ ID NO 2
<211> LENGTH: 1314
<212> TYPE: DNA
<213> ORGANISM: Coniochaeta sp.

<400> SEQUENCE: 2

```
atgacgtcga atcgtgcaga tacaagggtg attgtcgtcg gtggcggagg aacgattggt       60
tcctcgacag cgctgcatct tgtgaggagt ggttatgctc ccgcaaatat cacggtcttg      120
gacacatttg agattccatc ggctcaatca gccggccatg atctcaacaa gatcatggga      180
atacgactgc gcaacaaggt ggacctgcaa atgagtctag aggctagaca gatgtggaag      240
gaggatgagt tattccagcc cttctttcac aataccggca gaatggactg cgaacacacg      300
cctgagggta tcgaggacct gaaaaagcag taccaggcac tgcacgatgc cggtgcgggt      360
ctggagaaga ctcatgcctg gttggacaac gaggatgaga tcttatccaa gatgccgttg      420
cttcaacgtg accaaataca aggatggaaa gcaatatgga gtcaagatgg cggctggtta      480
gctgcggcaa aggccatcaa tgcgatcgga cagttcttga agaacgtgg tgtaaagttc      540
ggattcggcg acgctggatc cttcaagcaa ccccttttcg acgatgaagg cacaacttgc      600
attggcgttg agacggcaga tggtaccaaa tattacgctg acaaggtggt cttagcagct      660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg      780
tataatggcg aacttggctt cttctttgag cctgatgagt ttggtgtaat aaaggtgtgc      840
gacgagttcc caggattctc gcgcttcaag gaacatcaac cctatgcgc cccatctccg      900
aaacggatat cagtaccacg atcgcacgcc aagcatccca cagacactta tccagacgca      960
tccgaagtca gcatcaaaaa agcaatcgcg acgtttctcc ctcgatttca ggacaaggag     1020
ctcttcaatc gcgccttgtg ctggtgtaca gacactgcgg acgctgctct cttgatgtgt     1080
gaacacccca atggaagaa tttcattcta gcgaccggcg acagcggaca ctcattcaaa     1140
atcttgccta acgtcggaaa atacgtagtc gagttgatag agggccgcct gccggaggaa     1200
atggcttatc aatggaggtg gcggccagga ggcgatgcac tcaagtctag acgtgcggca     1260
ccgccaaaag atcttgcaga catgccagga tggaaacatg atccgaaatt gtaa           1314
```

<210> SEQ ID NO 3
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 3
caatcagccg gctatgatct caacaagatc                                        30

<210> SEQ ID NO 4
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 4
cagtcgtatt cccatgatct tgttgagat                                        29

<210> SEQ ID NO 5
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 5
aaggatggaa atgcatatgg aatcaag                                          27

<210> SEQ ID NO 6
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 6
ttgattccat atgcatttcc atccttg                                          27

<210> SEQ ID NO 7
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 7
gatggaaaca tgattaaaat ccatatgac                                        29

<210> SEQ ID NO 8
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 8
tcatatggat tttaatcatg tttccatcc                                        29

<210> SEQ ID NO 9
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 9
cttttcgacg atgatggcac aacttgcatt                                       30

<210> SEQ ID NO 10
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 10
tgccgtctca acgccaatgc aagttgtgcc                                       30

<210> SEQ ID NO 11
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 11
ccagacgcat ccgaagaaag catcaaaaaa                               30

<210> SEQ ID NO 12
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 12
ttcggatgcg tctggataag tgtctgt                                  27

<210> SEQ ID NO 13
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 13
ttgtgctggt gtgcggacac tgcggacgct                               30

<210> SEQ ID NO 14
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 14
acacatcaag agagcagcgt ccgcagtgtc                               30

<210> SEQ ID NO 15
<211> LENGTH: 438
<212> TYPE: PRT
<213> ORGANISM: Aspergillus fumigatus

<400> SEQUENCE: 15

Met Ala Val Thr Lys Ser Ser Leu Leu Ile Val Gly Ala Gly Thr
1               5                   10                  15

Trp Gly Thr Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Val Ile Ser Ser Gly Gln Tyr Ser Asn Asn Lys
        50                  55                  60

Asp Glu Ile Glu Val Asn Glu Ile Leu Ala Glu Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
        115                 120                 125

Gln Phe Arg Lys Leu Ala Pro Glu Gly Val Leu Gln Gly Asp Phe Pro
    130                 135                 140

Gly Trp Lys Gly Tyr Phe Ala Arg Ser Gly Ala Gly Trp Ala His Ala

```
            145                 150                 155                 160
Arg Asn Ala Leu Val Ala Ala Arg Glu Ala Gln Arg Met Gly Val
                    165                 170                 175

Lys Phe Val Thr Gly Thr Pro Gln Gly Arg Val Val Thr Leu Ile Phe
                180                 185                 190

Glu Asn Asp Val Lys Gly Ala Val Thr Gly Asp Gly Lys Ile Trp
                195                 200                 205

Arg Ala Glu Arg Thr Phe Leu Cys Ala Gly Ala Ser Ala Gly Gln Phe
            210                 215                 220

Leu Asp Phe Lys Asn Gln Leu Arg Pro Thr Ala Trp Thr Leu Val His
225                 230                 235                 240

Ile Ala Leu Lys Pro Glu Arg Ala Leu Tyr Lys Asn Ile Pro Val
                    245                 250                 255

Ile Phe Asn Ile Glu Arg Gly Phe Phe Glu Pro Asp Glu Arg
                260                 265                 270

Gly Glu Ile Lys Ile Cys Asp Glu His Pro Gly Tyr Thr Asn Met Val
                275                 280                 285

Gln Ser Ala Asp Gly Thr Met Met Ser Ile Pro Phe Glu Lys Thr Gln
            290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                    325                 330                 335

Cys Ala Asp Thr Ala Asn Arg Glu Phe Leu Ile Asp Arg His Pro Gln
                340                 345                 350

Tyr His Ser Leu Val Leu Gly Cys Gly Ala Ser Gly Arg Gly Phe Lys
                355                 360                 365

Tyr Leu Pro Ser Ile Gly Asn Leu Ile Val Asp Ala Met Glu Gly Lys
            370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Pro Asn
                    405                 410                 415

Arg Val Met Asp Phe His Asp Val Lys Glu Trp Thr Asn Val Gln Tyr
                420                 425                 430

Arg Asp Ile Ser Lys Leu
            435

<210> SEQ ID NO 16
<211> LENGTH: 437
<212> TYPE: PRT
<213> ORGANISM: Eupenicillium terrenum

<400> SEQUENCE: 16

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
                20                  25                  30

Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
        50                  55                  60

Asn Gly Pro Asp Leu Gln Leu Ser Leu Glu Ser Leu Asp Met Trp Gln
65                  70                  75                  80
```

```
Asn Asp Glu Leu Phe Lys Pro Phe Phe His Gln Val Gly Met Ile Asp
                 85                  90                  95
Cys Ser Ser Lys Glu Gly Ile Glu Asn Leu Arg Arg Lys Tyr Gln
            100                 105                 110
Thr Leu Leu Asp Ala Gly Ile Gly Leu Glu Lys Thr Asn Val Trp Leu
            115                 120                 125
Glu Ser Glu Asp Glu Ile Leu Ala Lys Ala Pro Asn Phe Thr Arg Glu
            130                 135                 140
Gln Val Lys Gly Trp Lys Gly Leu Phe Cys Thr Asp Gly Gly Trp Leu
145                 150                 155                 160
Ala Ala Ala Lys Ala Ile Asn Ala Ile Gly Ile Phe Leu Gln Asp Lys
                165                 170                 175
Gly Val Lys Phe Gly Phe Gly Asp Ala Gly Thr Phe Gln Gln Pro Leu
            180                 185                 190
Phe Ala Ala Asp Gly Lys Thr Cys Ile Gly Leu Glu Thr Thr Asp Gly
            195                 200                 205
Thr Lys Tyr Phe Ala Asp Lys Val Val Leu Ala Ala Gly Ala Trp Ser
    210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
                245                 250                 255
Val Pro Val Val Tyr Asp Gly Glu Tyr Gly Phe Phe Phe Glu Pro Asp
            260                 265                 270
Glu Tyr Gly Val Ile Lys Val Cys Asp Glu Phe Pro Gly Phe Ser Arg
    275                 280                 285
Phe Lys Leu His Gln Pro Tyr Gly Ala Ala Ser Pro Lys Met Ile Ser
    290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
                325                 330                 335
Lys Asp Lys Glu Leu Phe Asn Arg Thr Met Cys Trp Cys Thr Asp Thr
            340                 345                 350
Ala Asp Ala Asn Leu Leu Ile Cys Glu His Pro Lys Trp Lys Asn Phe
            355                 360                 365
Ile Leu Ala Thr Gly Asp Ser Gly His Ser Phe Lys Leu Leu Pro Asn
    370                 375                 380
Ile Gly Lys Tyr Val Val Glu Leu Leu Glu Gly Ser Leu Ser Gln Glu
385                 390                 395                 400
Met Ala Gly Ala Trp Arg Trp Arg Pro Gly Gly Asp Ala Leu Arg Ser
                405                 410                 415
Arg Arg Gly Ala Pro Ala Lys Asp Leu Ala Glu Met Pro Gly Trp Lys
            420                 425                 430
His Asp Ala His Leu
            435

<210> SEQ ID NO 17
<211> LENGTH: 1314
<212> TYPE: DNA
<213> ORGANISM: Eupenicillium terrenum

<400> SEQUENCE: 17
atggctcatt cgcgtgcaag caccaaagtc gtcgtggttg ggggaggtgg tacgatcggg      60
```

```
tcttcgacgg ctctgcactt aatccgctct ggatataccc cctcaaatat caccgtgctt    120
gacgtataca agacccttc attgcaatct gcaggacatg atttgaacaa gatcatgggc    180
attcgattgc gcaacgggcc tgacttgcag cttcgctgg aatcactcga catgtggcaa    240
aacgatgagt tgttcaagcc attctttcac caagtgggca tgattgattg ttcgtcatcc    300
aaagagggta ttgaaaatct tcgacgaaaa taccagaccc tcctcgatgc gggcattggg    360
ctggagaaga cgaacgtttg gctggaatct gaagatgaga tcctcgccaa agcgccgaat    420
ttcacgcgtg aacaagtcaa ggggtggaaa ggcttatttt gcactgatgg aggctggctt    480
gctgcagcca aggctatcaa tgcgatcgga atttcctcc aggacaaagg tgtcaagttt    540
ggctttggag atgctggaac atttcagcaa cctctgttcg ccgctgatgg aaaaacttgc    600
atcggacttg aaactacaga cggaaccaag tactttgctg acaaggttgt cttggctgct    660
ggtgcgtgga gtcccacctt ggtggatcta aagatcagt gtgtttcaaa ggcctgggtt    720
ttcgctcata ttcaactcac acccaaagaa gcggacgcgt acaagaatgt gcctgtggtc    780
tatgatggtg aatatgggtt ctttttgag cccgacgagt atggggtgat caaagtctgt    840
gacgagttcc ctggtttctc tcgcttcaaa ctgcatcaac cgtacggggc tgcatctccc    900
aagatgatat ccgtaccgcg atcacacgcc aagcatccca cagataccta ccctgatgcc    960
tccgaagtca ccatacgcaa agcgatcgca aggttcctgc cagaatttaa agacaaggag    1020
ctcttcaacc gtaccatgtg ctggtgtaca gatacggccg atgctaactt attgatttgc    1080
gaacacccga gtggaagaa tttcattctg gccactggag atagcggaca ttccttcaag    1140
ctgttgccaa acatcgggaa atacgttgtt gagcttttag agggatctct atcgcaggaa    1200
atggctggtg cctggagatg gagacccgga ggtgatgctc ttagatctag acgcggtgct    1260
ccggcaaagg atcttgctga gatgccggga tggaagcatg atgcacattt gtga           1314
```

<210> SEQ ID NO 18
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 18
aaggggtgga aatgcttatt ttgcactgat                                      30

<210> SEQ ID NO 19
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 19
agcaagccag cctccatcag tgcaaaataa                                      30

<210> SEQ ID NO 20
<211> LENGTH: 437
<212> TYPE: PRT
<213> ORGANISM: Phaeosphaeria nodorum

<400> SEQUENCE: 20

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

```
Thr Pro Ser Asn Val Thr Val Leu Asp Ala Tyr Pro Ile Pro Ser Ser
         35                  40                  45

Gln Ser Ala Gly Asn Asp Leu Asn Lys Ile Met Gly Val Ser Leu Arg
 50                  55                  60

Asn Pro Val Asp Leu Gln Leu Ala Leu Glu Ala Arg Gln Met Trp Asn
 65                  70                  75                  80

Glu Asp Glu Leu Phe Lys Lys Phe Phe His Asn Thr Gly Arg Leu Asp
                 85                  90                  95

Cys Ala His Gly Glu Lys Asp Ile Ala Asp Leu Lys Ser Gly Tyr Gln
                100                 105                 110

Ala Leu Val Asp Ala Gly Leu Asp Ala Thr Asn Glu Trp Leu Asp Ser
            115                 120                 125

Glu Asp Glu Ile Leu Lys Arg Met Pro Leu Leu Ser Arg Asp Gln Ile
            130                 135                 140

Lys Gly Trp Lys Ala Ile Phe Ser Lys Asp Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
            195                 200                 205

Ala Asp Lys Val Val Leu Ala Ala Gly Ala Trp Ser Pro Thr Leu Val
210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
            290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
            370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
            435
```

<210> SEQ ID NO 21
<211> LENGTH: 1314
<212> TYPE: DNA
<213> ORGANISM: Phaeosphaeria nodorum

<400> SEQUENCE: 21

| | | | | | |
|---|---|---|---|---|---|
| atggcccgt | cgcgtgctaa | tacgtcggtc | attgtggttg | gtggtggtgg | tacgattggc | 60 |
| tcatctacgg | ctctgcatct | ggtccgctca | ggctataccc | cgtcgaacgt | gacggttctg | 120 |
| gatgcatacc | cgattccgag | ctctcagagc | gctggcaacg | acctgaataa | aatcatgggt | 180 |
| gtctctctgc | gtaatccggt | ggatctgcag | ctggctctgg | aagcgcgcca | aatgtggaac | 240 |
| gaagacgaac | tgttcaagaa | gttttttccat | aacaccggcc | gtctggattg | cgcgcacggt | 300 |
| gaaaaagata | ttgccgacct | gaagagcggc | tatcaggctc | tggtggatgc | gggtctggac | 360 |
| gccacgaacg | aatggctgga | tagtgaagac | gaaatcctga | acgtatgcc | gctgctgtcc | 420 |
| cgcgatcaaa | ttaaaggctg | gaaggcgatc | ttttcaaaag | acggtggttg | gctggcagca | 480 |
| gcaaaggcaa | ttaatgcagt | tggtgaatat | ctgcgtgatc | agggcgtccg | cttcggtttt | 540 |
| tacggcgccg | gttctttcaa | agcaccgctg | ctggctgaag | gcgtctgcat | cggtgtcgaa | 600 |
| accgtggatg | gcacgcgcta | ttacgcagac | aaagtggttc | tggctgcagg | tgcatggtcg | 660 |
| ccgaccctgg | ttgaactgca | tgaacagtgt | gtgagcaaag | cgtgggttta | cggccacatt | 720 |
| caactgacgc | cggaagaagc | cgcacgttat | aagaacagcc | cggtcgtgta | caatggcgat | 780 |
| gtgggctttt | tctttgaacc | gaacgaacat | ggcgttatca | agtctgcga | tgaatttccg | 840 |
| ggttttaccc | gcttcaagat | gcaccagccg | tttggtgcca | agcaccgaa | gcgtattagt | 900 |
| gtgccgcgct | cccatgccaa | acacccgacc | gatacgatcc | cggatgcaag | tgacgtttcc | 960 |
| attcgtcgcg | ctatcgcgac | ctttatgccg | cagttcaaga | acaaaaagat | gttcaaccaa | 1020 |
| gcgatgtgct | ggtgtaccga | tacggccgac | gctgcgctgc | tgatttgtga | acatccggaa | 1080 |
| tggaaaaact | ttgttctggc | gaccggcgat | tcaggtcatt | cgttcaaact | gctgccgaat | 1140 |
| atcggcaagc | acgttgtcga | actgctggag | ggtacgctgg | cagatgacct | ggcacacgca | 1200 |
| tggcgttggc | gtccgggtag | tggtgatgca | ctgaaaagcc | gtcgctctgc | tccggcgaaa | 1260 |
| gacctggctg | atatgccggg | ctggaaccat | gacaaaccgc | gtgctaatct | gtaa | 1314 |

<210> SEQ ID NO 22
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 22
aaaggctgga agtgcatctt ttcaaaagac                                    30

<210> SEQ ID NO 23
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 23
tgccagccaa ccaccgtctt ttgaaaagat                                    30

<210> SEQ ID NO 24
<211> LENGTH: 29

-continued

<212> TYPE: DNA
<213> ORGANISM: Artificial Sequence
<220> FEATURE:
<223> OTHER INFORMATION: Artificially Synthesized Primer Sequence

<400> SEQUENCE: 24
taaattgggt catcggatcc cgggcccgt                                      29

<210> SEQ ID NO 25
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 25
acgcggtttg tcatggttcc agcccggcat                                     30

<210> SEQ ID NO 26
<211> LENGTH: 440
<212> TYPE: PRT
<213> ORGANISM: Pyrenochaeta sp.

<400> SEQUENCE: 26

Met Ala Ala Ser Arg Ala Lys Thr Thr Val Ile Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gly Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

```
Gly Val Ile Lys Val Cys Asp Glu Phe Pro Gly Phe Thr Arg Phe Lys
            275                 280                 285

Lys His Gln Pro Phe Gly Ala Arg Ala Pro Lys Arg Ile Ser Val Pro
    290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
                340                 345                 350

Ala Ala Leu Leu Ile Cys Glu His Pro Gln Trp Lys Asn Phe Met Leu
            355                 360                 365

Ala Thr Gly Asp Ser Gly His Ser Phe Lys Leu Leu Pro Asn Ile Gly
        370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
                420                 425                 430

Asp Glu Ser Pro Arg Ala Lys Leu
            435                 440

<210> SEQ ID NO 27
<211> LENGTH: 452
<212> TYPE: PRT
<213> ORGANISM: Arthrinium sp.

<400> SEQUENCE: 27

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
                20                  25                  30

Thr Ala Thr Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
```

```
                    195                 200                 205
Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365

Phe Ile Leu Ala Thr Gly Asp Ser Gly His Ser Phe Lys Leu Leu Pro
    370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450

<210> SEQ ID NO 28
<211> LENGTH: 440
<212> TYPE: PRT
<213> ORGANISM: Curvularia clavata

<400> SEQUENCE: 28

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110
```

```
Ala Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Asp Arg Glu
        130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
        275                 280                 285

Gln His Gln Pro Tyr Gly Ala Lys Ala Pro Lys Arg Ile Ser Val Pro
290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Pro Ala Lys Asp Leu Ala Asp Met Pro Gly Trp Lys His
            420                 425                 430

Asp Asp Val Val Lys Ser Lys Leu
            435                 440

<210> SEQ ID NO 29
<211> LENGTH: 441
<212> TYPE: PRT
<213> ORGANISM: Neocosmospora vasinfecta

<400> SEQUENCE: 29

Met Thr Thr Pro Arg Lys Glu Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45
```

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
                100                 105                 110

Lys Leu Val Glu Ala Gly Val Gly Leu Glu Glu Thr His Glu Trp Leu
            115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Ala Gly Ser Phe Lys Arg Pro Leu
                180                 185                 190

Phe Ala Asp Asp Gly Thr Thr Cys Ile Gly Val Glu Thr Val Asp Gly
            195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Val Tyr Lys Gly
                245                 250                 255

Cys Pro Val Val Tyr His Gly Asp Val Gly Phe Phe Phe Glu Pro Asn
                260                 265                 270

Glu Asn Gly Val Ile Lys Val Cys Asp Glu Phe Pro Gly Phe Thr Arg
            275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
    355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
            435                 440

<210> SEQ ID NO 30
<211> LENGTH: 477

```
<212> TYPE: PRT
<213> ORGANISM: Cryptococcus neoformans

<400> SEQUENCE: 30

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400
```

```
Leu Ala Glu Ser Trp Arg Trp Arg Pro Gly Ser Gly Asp Pro Leu Ile
            405                 410                 415

Ser Arg Arg Ala Ala Pro Ala Arg Asp Leu Ala Asp Leu Pro Gly Trp
                420                 425                 430

Asn His Asp Glu Pro Ser Asp Asp Asp Met Asp Val Lys Asp Val Ala
                435                 440                 445

Val Ser Leu Ala Ser Val Lys Ile Gly Glu Asn Ile Gly Glu Lys Val
450                 455                 460

Val Glu Asp Gly Ala Arg Val Gly Val Lys Val Leu Ala
465                 470                 475

<210> SEQ ID NO 31
<211> LENGTH: 438
<212> TYPE: PRT
<213> ORGANISM: Aspergillus nidulans

<400> SEQUENCE: 31

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Cys Pro Ile Pro Ser Ala Gln
                35                  40                  45

Ser Ala Gly Tyr Asp Leu Asn Lys Ile Met Ser Ile Arg Leu Arg Asn
            50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
                100                 105                 110

Leu Leu Asp Ala Gly Ile Gly Leu Glu Lys Thr Asn Phe Met Leu Glu
            115                 120                 125

Ser Glu Asp Glu Ile Leu Ala Lys Ala Pro His Phe Thr Gln Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Glu Pro Asn
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Ala Pro Lys Pro Ile Ser
```

```
                290                 295                 300
Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 32
<211> LENGTH: 441
<212> TYPE: PRT
<213> ORGANISM: Ulocladium sp.

<400> SEQUENCE: 32

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220
```

```
Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
            245                 250                 255

Val Val Tyr Asn Gly Asp Val Gly Phe Phe Glu Pro Asp Glu Tyr
        260                 265                 270

Gly Val Ile Lys Val Cys Asp Glu Phe Pro Gly Phe Thr Arg Phe Lys
            275                 280                 285

Gln His Gln Pro Phe Gly Ala Ser Ala Pro Lys Arg Ile Ser Val Pro
        290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
            325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
            420                 425                 430

Asp Gly Glu Ala Pro Arg Ala Lys Leu
        435                 440

<210> SEQ ID NO 33
<211> LENGTH: 437
<212> TYPE: PRT
<213> ORGANISM: Penicillium crysogenum

<400> SEQUENCE: 33

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Trp Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Ala Arg Glu
    130                 135                 140

Gln Ile Lys Gly Trp Lys Gly Leu Phe Cys Gly Asp Gly Gly Trp Leu
145                 150                 155                 160
```

-continued

```
Ala Ala Ala Lys Ala Ile Asn Ala Ile Gly Thr Phe Leu Lys Ser Gln
            165             170             175
Gly Val Lys Phe Gly Phe Gly Ser Ala Gly Thr Phe Lys Arg Pro Leu
            180             185             190
Phe Ala Pro Asp Gly Ala Thr Cys Ser Gly Val Glu Thr Val Asp Gly
            195             200             205
Thr Lys Tyr Phe Ala Asp Lys Val Val Leu Ala Ala Gly Ala Trp Ser
            210             215             220
Ser Thr Leu Val Asp Leu Glu Asp Gln Cys Val Ser Lys Ala Trp Val
225             230             235             240
Phe Ala His Ile Gln Leu Thr Pro Gln Glu Ser Ala Gln Tyr Lys Asp
            245             250             255
Val Pro Val Val Tyr Asp Gly Asp Tyr Gly Phe Phe Phe Glu Pro Asn
            260             265             270
Glu His Gly Val Ile Lys Val Cys Asp Glu Phe Pro Gly Phe Ser Arg
            275             280             285
Phe Lys Leu His Gln Pro Tyr Gly Ala Thr Ser Pro Lys Leu Ile Ser
            290             295             300
Val Pro Arg Ser His Ala Lys His Pro Thr Asp Thr Tyr Pro Asp Ser
305             310             315             320
Ser Glu Glu Thr Ile Arg Lys Ala Ile Ala Arg Phe Met Pro Arg Phe
            325             330             335
Lys Asp Lys Glu Leu Phe Asn Arg Ser Met Cys Trp Cys Thr Asp Thr
            340             345             350
Ala Asp Ala Asn Leu Leu Ile Cys Glu His Pro Lys Trp Lys Asn Phe
            355             360             365
Ile Leu Ala Thr Gly Asp Ser Gly His Ser Phe Lys Val Leu Pro Asn
            370             375             380
Ile Gly Lys His Val Val Glu Leu Ile Glu Gly Arg Leu Pro Gln Asp
385             390             395             400
Leu Ala Gly Ala Trp Arg Trp Arg Pro Gly Gly Asp Ala Leu Lys Ser
            405             410             415
Lys Arg Ser Ala Pro Ala Lys Asp Leu Ala Glu Met Pro Gly Trp Lys
            420             425             430
His Asp Ala Lys Leu
            435
```

AMADORIASE WITH IMPROVED THERMOSTABILITY, GENE AND RECOMBINANT DNA FOR THE AMADORIASE, AND METHOD FOR PRODUCTION OF AMADORIASE WITH IMPROVED THERMOSTABILITY

CROSS-REFERENCE TO RELATED APPLICATION

This application is a United States national phase application of International Application PCT/JP2012/083779 filed Dec. 27, 2012.

TECHNICAL FIELD

The present invention relates to an amadoriase having superior heat resistance able to be advantageously used as a diagnostic enzyme for diabetes or in a diabetes marker assay kit, a gene and recombinant DNA thereof, and a method for producing an amadoriase having superior heat resistance.

BACKGROUND ART

Glycated proteins are formed by an amadori rearrangement following non-enzymatic covalent bond formation by an aldehyde group of an aldose such as glucose (monosaccharide having a latent aldehyde group and derivatives thereof) and an amino group of the protein. Examples of protein amino groups include α-amino groups on the amino terminal and ε-amino groups on a lysine residue side chain in a protein. Known examples of glycated proteins formed in the body include glycated hemoglobin formed by the glycation of hemoglobin in blood and glycated albumin formed by the glycation of albumin.

Among these glycated proteins formed in the body, glycated hemoglobin (HbA1c) is attracting attention in diabetes and other clinical diagnostic fields as an important blood sugar control marker for diagnosing and managing the symptoms of diabetes patients. HbA1c concentration in blood reflects an average blood sugar value over a prior fixed period of time, and measured values thereof serve as important indicators in the diagnosis and management of the symptoms of diabetes.

An enzymatic method using amadoriase has been proposed as a method for rapidly and easily measuring HbA1c levels, and more specifically, consists of decomposition of HbA1c by an enzyme such as protease followed by quantification of α-fructosyl valyl histidine (to be represented by "αFVH") or α-fructosyl valine (to be represented by "αFV") isolated from the β-chain amino terminal thereof (see, for example, Patent Documents 1 to 7). In actuality, methods for cleaving αFV from HbA1c are considerably affected by contaminants and the like and have the problem of being unable to obtain accurate measured values, and consequently, current methods at present consist mainly of measurement of αFVH for the purpose of obtaining more accurate measured values.

Amadoriase catalyzes a reaction that forms glyoxylic acid or α-ketoaldehyde, amino acid or peptide, and hydrogen peroxide by oxidizing iminodiacetic acid or a derivative thereof (also referred to as an "amadori compound") in the presence of oxygen.

Although amadoriase is found in bacteria, yeasts and fungi, reported examples of amadoriases that are particularly useful in the measurement of HbA1c as a result of having enzymatic activity on αFVH and/or αFV include amadoriases derived from *Coniochaeta* species, *Eupenicillium* species, *Pyrenochaeta* species, *Arthrinium* species, *Curvularia* species, *Neocosmospora* species, *Cryptococcus* species, *Phaeosphaeria* species, *Aspergillus* species, *Emericella* species, *Ulocladium* species, *Penicillium* species, *Fusarium* species, *Achaetomiella* species, *Achaetomium* species, *Thielavia* species, *Chaetomium* species, *Gelasinospora* species, *Microascus* species, *Leptosphaeria* species, *Ophiobolus* species, *Pleospora* species, *Coniochaetidium* species, *Pichia* species, *Corynebacterium* species, *Agrobacterium* species and *Arthrobacter* species (see, for example, Patent Documents 1 and 6 to 15 and Non-Patent Documents 1 to 11). Furthermore, among the aforementioned reported examples, amadoriase may also be referred to using expressions such as ketoamine oxidase, fructosyl amino acid oxidase, fructosyl peptide oxidase or fructosyl amine oxidase depending on the literature.

Favorable thermal stability is one example of a property of amadoriase that is desirable in terms of formulation in a kit reagent for use as an enzyme for clinical diagnosis of diabetes.

Although actual measurement conditions vary according to individual strains, disclosures relating to the thermal stability of various types of amadoriase are found in the known literature. Namely, fungal amadoriase derived from *Aspergillus terreus* strain GP1 demonstrates residual activity of about 40% following heat treatment at 45° C. for 10 minutes (see, for example, Non-Patent Document 4). Fungal amadoriase derived from *Fusarium oxysporum* strain S-1F4 demonstrates residual activity of about 10% following heat treatment at 45° C. for 5 minutes (see, for example, Non-Patent Document 12). In addition, fungal amadoriase derived from *Coniochaetidium savoryi* strain ATCC 36547 demonstrates residual activity of about 80% following heat treatment at 37° C. for 10 minutes (see, for example, Patent Document 9). Each of the fungal amadoriases derived from *Arthrinium* sp. strain T06, *Pyrenochaeta* sp. strain YH807, *Leptosphaeria nodorum* strain NBRC 7480, *Pleospora herbarum* strain NBRC 32012 and *Ophiobolus herpotrichus* strain NBRC 6158 demonstrates residual activity of 80% following heat treatment at 40° C. for 30 minutes (see, for example, Patent Document 9). Fungal amadoriase derived from *Neocosmospora vasinfecta* strain NBRC 7590 demonstrates residual activity of 80% following heat treatment at 45° C. for 30 minutes (see, for example, Patent Document 9). Fungal amadoriase derived from *Curvularia clavata* strain YH923 demonstrates residual activity of 80% following heat treatment at 50° C. for 30 minutes (see, for example, Patent Document 9). Amadoriase derived from *Cryptococcus neoformans* lacking 34 to 39 amino acid residues of the carboxyl terminal region demonstrates residual activity of 40% following heat treatment at 45° C. for 10 minutes (see, for example, Patent Document 12). Amadoriase derived from *Eupenicillium terrenum* strain ATCC 18547 or *Coniochaeta* sp. strain NISL 9330 demonstrates residual activity of 80% or more at 45° C. for 10 minutes (see, for example, Patent Document 8).

Heat-resistant amadoriases have also been proposed that demonstrate further improved thermal stability as a result of substituting several amino acids of the aforementioned amadoriase proteins. More specifically, reported examples thereof include amadoriase derived from mutant *Coniochaeta* sp. strain NISL 9330, amadoriase derived from mutant *Eupenicillium terrenum* strain ATCC 18547, amadoriase derived from a mutant *Aspergillus nidulans* strain, and amadoriase derived from a mutant *Phaeosphaeria* strain (see, for example, Patent Documents 16 and 17). In particular, the mutant amadoriase produced by *Escherichia coli* strain JM109 (pKK223-3-CFP-T9) disclosed in Patent Document 16 (to be represented by "CFP-T9") demonstrates extremely superior thermal stability in comparison with conventional amadoriases, and has been shown to maintain residual activity of 100% even after heat treatment at 50° C. for 60 minutes. In addition, the mutant amadoriase IE353-F282Y derived from *Phaeosphaeria nodorum* disclosed in Patent Document 17 has been shown to maintain residual activity of 92% following heat treatment at 50° C. for 10 minutes.

However, in the case of presuming a kit incorporating an enzyme being subjected to increasingly severe temperature conditions such as during distribution at ambient temperatures or long-distance transport, or in the case of considering applications such as an enzyme sensor which are presumed to be subjected to heat treatment in a manufacturing process, there continues to be a strong demand for enzymes having even more superior heat resistance and further improved heat resistance than the amadoriases that have been proposed thus far. Such heat-resistant enzymes are expected to make a significant contribution in the fields of enzyme and enzyme kit distribution as well as the development of sensors and other applications.

PRIOR ART DOCUMENTS

Patent Documents

Patent Document 1: International Patent Publication No. WO 2004/104203
Patent Document 2: International Patent Publication No. WO 2005/49857
Patent Document 3: Japanese Unexamined Patent Publication No. 2001-95598
Patent Document 4: Japanese Examined Patent Publication No H05-33997
Patent Document 5: Japanese Unexamined Patent Publication No. H11-127895
Patent Document 6: International Patent Publication No. WO 97/13872
Patent Document 7: Japanese Unexamined Patent Publication No. 2011-229526
Patent Document 8: Japanese Patent No. 4231668
Patent Document 9: Japanese Unexamined Patent Publication No. 2004-275013
Patent Document 10: Japanese Unexamined Patent Publication No. 2004-275063
Patent Document 11: Japanese Unexamined Patent Publication No. 2010-35469
Patent Document 12: Japanese Unexamined Patent Publication No. 2010-57474
Patent Document 13: International Patent Publication No. WO 2010/41715
Patent Document 14: International Patent Publication No. WO 2010/41419
Patent Document 15: International Patent Publication No. WO 2011/15325
Patent Document 16: International Patent Publication No. WO 2007/125779
Patent Document 17: Japanese Unexamined Patent Publication No. 2010-115189

Non-Patent Documents

Non-Patent Document 1: Biochem. Biophys. Res. Commun., 311, 104-11, 2003
Non-Patent Document 2: Biotechnol. Bioeng., 106, 358-66, 2010
Non-Patent Document 3: J. Biosci. Bioeng., 102, 241-3, 2006
Non-Patent Document 4: Eur. J. Biochem., 242, 499-505, 1996
Non-Patent Document 5: Arch. Microbiol., 178, 344-50, 2002
Non-Patent Document 6: Mar. Biotechnol., 6, 625-32, 2004
Non-Patent Document 7: Biosci. Biotechnol. Biochem., 59, 487-91, 1995
Non-Patent Document 8: Appl. Microbiol. Biotechnol., 74, 813-819, 2007
Non-Patent Document 9: Biosci. Biotechnol. Biochem., 66, 1256-61, 2002
Non-Patent Document 10: Biosci. Biotechnol. Biochem., 66, 2323-29, 2002
Non-Patent Document 11: Biotechnol. Letters, 27, 27-32, 2005
Non-Patent Document 12: Biosci. Biotechnol. Biochem., 59, 487-91, 1995

DISCLOSURE OF THE INVENTION

Problems to be Solved by the Invention

An object of the present invention is to provide an amadoriase having thermal stability that is superior to that of conventional amadoriases.

Means for Solving the Problems

As a result of conducting extensive studies in an attempt to acquire a mutant having even more improved heat resistance based on the aforementioned CFP-T9 previously found by the applicant, the inventors of the present invention found that the aforementioned object can be achieved by introducing a specific amino acid residue substitution and/or deletion, thereby leading to completion of the present invention.

Namely, the present invention is as described below.

(1) An amadoriase having an amino acid sequence introduced with one or more deletions, insertions, additions and substitutions of one or a plurality of amino acids in the amino acid sequence indicated in SEQ ID NO: 1, and having a substitution or deletion of one or more amino acid residues at a position corresponding to an amino acid selected from the group consisting of the following (a) to (j) of the amino acid sequence indicated in SEQ ID NO: 1:
  (a) three amino acid residues from the carboxyl terminal,
  (b) alanine at position 151,
  (c) phenylalanine at position 43,
  (d) histidine at position 53,
  (e) phenylalanine at position 267,
  (f) threonine at position 350,
  (g) alanine at position 185,
  (h) glutamic acid at position 196,
  (i) serine at position 299, and
  (j) valine at position 323; wherein,
residual activity (%) following heat treatment at 55° C. for 30 minutes at pH 7.0 is improved in comparison with amadoriase prior to the substitution.

(2) An amadoriase having an amino acid sequence in which:

an amino acid of the amino acid sequence indicated in SEQ ID NO: 1:

(k) has three amino acid residues deleted from the carboxyl terminal, or is substituted with an amino acid residue as described in any of the following (l) to (t):

(l) alanine at position 151 is substituted with cysteine, (m) phenylalanine at position 43 is substituted with tyrosine, (n) histidine at position 53 is substituted with asparagine or tyrosine, (o) phenylalanine at position 267 is substituted with tyrosine, (p) threonine at position 350 is substituted with alanine, (q) alanine at position 185 is substituted with serine, (r) glutamic acid at position 196 is substituted with aspartic acid, (s) serine at position 299 is substituted with threonine, and (t) valine at position 323 is substituted with glutamic acid; and, one or more deletions, insertions, additions and substitutions of several amino acids are introduced at positions other than the positions having the substitution or deletion; wherein, residual activity following heat treatment at 55° C. for 30 minutes at pH 7.0 is improved in comparison with amadoriase prior to the substitution or deletion.

(3) An amadoriase having a substitution or deletion of amino acid residues in the amino acid sequence indicated in SEQ ID NO: 1 selected from the group consisting of the following (u) to (ae):

(u) substitution of the amino acid at the position corresponding to alanine at position 151 with cysteine and substitution of the amino acid at the position corresponding to serine at position 299 with threonine, (v) substitution of the amino acid at the position corresponding to phenylalanine at position 43 with tyrosine and substitution of the amino acid at the position corresponding to alanine at position 151 with cysteine, (w) substitution of the amino acid at the position corresponding to phenylalanine at position 43 with tyrosine and deletion of the amino acid residues at the positions corresponding to the three amino acid residues from the carboxyl terminal, (x) substitution of the amino acid at the position corresponding to alanine at position 151 with cysteine, substitution of the amino acid at the position corresponding to glutamic acid at position 196 with aspartic acid, and substitution of the amino acid at the position corresponding to serine at position 299 with threonine, (y) substitution of the amino acid at the position corresponding to alanine at position 151 with cysteine, substitution of the amino acid at the position corresponding to serine at position 299 with threonine, and deletion of the amino acid residues at the positions corresponding to the three amino acid residues from the carboxyl terminal, (z) substitution of the amino acid at the position corresponding to phenylalanine at position 43 with tyrosine, substitution of the amino acid at the position corresponding to threonine at position 350 with alanine, and deletion of the amino acid residues at the positions corresponding to the three amino acid residues from the carboxyl terminal, (aa) substitution of the amino acid at the position corresponding to phenylalanine at position 43 with tyrosine, substitution of the amino acid at the position corresponding to alanine at position 151 with cysteine, and deletion of the amino acid residues at the positions corresponding to the three amino acid residues from the carboxyl terminal, (ab) substitution of the amino acid at the position corresponding to phenylalanine at position 43 with tyrosine, substitution of the amino acid at the position corresponding to alanine at position 151 with cysteine, and substitution of the amino acid at the position corresponding to threonine at position 350 with alanine, (ac) substitution of the amino acid at the position corresponding to alanine at position 151 with cysteine, substitution of the amino acid at the position corresponding to glutamic acid at position 196 to aspartic acid, substitution of the amino acid at the position corresponding to serine at position 299 with threonine, and substitution of the amino acid at the position corresponding to valine at position 323 with glutamic acid, (ad) substitution of the amino acid at the position corresponding to alanine at position 151 with cysteine, substitution of the amino acid at the position corresponding to glutamic acid at position 196 with aspartic acid, substitution of the amino acid at the position corresponding to serine at position 299 with threonine, and deletion of the amino acid residues at the positions corresponding to the three amino acid residues from the carboxyl terminal, and (ae) substitution of the amino acid at the position corresponding to phenylalanine at position 43 with tyrosine, substitution of the amino acid at the position corresponding to alanine at position 151 with cysteine, substitution of the amino acid at the position corresponding to threonine at position 350 with alanine, and deletion of the amino acid residues at the positions corresponding to the three amino acid residues from the carboxyl terminal, and having an amino acid sequence introduced with one or more deletions, insertions, additions and substitutions of several amino acids at positions other than the positions having the substitution or deletion; wherein, residual activity following heat treatment at 60° C. for 30 minutes at pH 7.0 is improved in comparison with amadoriase prior to the substitution or deletion.

(4) An amadoriase gene encoding the amino acid sequence described in any of (1) to (3) above.

(5) A recombinant vector containing the amadoriase gene described in (4) above.

(6) A host cell containing the recombinant vector described in (5) above.

(7) A method for producing amadoriase, comprising the following steps:

(i) a step for culturing the host cells described in (6) above, (ii) a step for expressing amadoriase gene contained in the host cells, and (iii) a step for isolating amadoriase from the culture.

(8) A kit for use in measuring a glycated protein, containing the amadoriase described in any of (1) to (3) above.

(9) A kit for use in measuring glycated hemoglobin, containing the amadoriase described in any of (1) to (3) above.

Effects of the Invention

According to the present invention, an amadoriase having superior thermal stability able to be advantageously used as an enzyme for diagnosing diabetes or in a diabetes marker assay kit, and a gene that encodes the same, can be provided.

BRIEF DESCRIPTION OF THE DRAWINGS

FIG. 1 shows an alignment of amino acid sequences of various types of known amadoriases.

BEST MODE FOR CARRYING OUT THE INVENTION

The following provides a detailed explanation of the present invention.

(Amadoriase)

Amadoriase, which is also referred to using such terms as ketoamine oxidase, fructosyl amino acid oxidase, fructosyl peptide oxidase or fructosyl amine oxidase, refers to an enzyme that catalyzes a reaction that forms glyoxylic acid or α-ketoaldehyde, amino acid or peptide, and hydrogen peroxide by oxidizing iminodiacetic acid or a derivative thereof (also referred to as an "amadori compound") in the presence of oxygen. Amadoriase is widely distributed throughout nature, and can be obtained by searching among enzymes originating in microorganisms, animals or plants. In microorganisms, amadoriase can be obtained from, for examples, molds, yeasts or bacteria.

One aspect of the amadoriase of the present invention is an amadoriase mutant having improved thermal stability that is produced based on amadoriase derived from *Coniochaeta* species having the amino acid sequence indicated in SEQ ID NO: 1. Examples of such mutants include amadoriases having an amino acid sequence having high sequence identity with SEQ ID NO: 1 (such as identity of 75% or more, preferably 80% or more, more preferably 85% or more, even more preferably 90% or more, still more preferably 95% or more, even more preferably still 97% or more, and most preferably 99% or more), and amadoriases having an amino acid sequence in which one to several amino acids in the amino acid sequence indicated in SEQ ID NO: 1 have been modified or mutated, or deleted, substituted, added and/or inserted. Furthermore, the amadoriase may also be produced based on amadoriase derived from other microorganisms provided conditions relating to thermal stability and/or amino acid sequence described in the claims are satisfied, and examples thereof include *Eupenicillium* species, *Pyrenochaeta* species, *Arthrinium* species, *Curvularia* species, *Neocosmospora* species, *Cryptococcus* species, *Phaeosphaeria* species, *Aspergillus* species, *Emericella* species, *Ulocladium* species, *Penicillium* species, *Fusarium* species, *Achaetomiella* species, *Achaetomium* species, *Thielavia* species, *Chaetomium* species, *Gelasinospora* species, *Microascus* species, *Leptosphaeria* species, *Ophiobolus* species, *Pleospora* species, *Coniochaetidium* species, *Pichia* species, *Corynebacterium* species, *Agrobacterium* species and *Arthrobacter* species.

A mutant (variant) of amadoriase having modified thermal stability can be obtained by substituting, adding or deleting at least one amino acid residue in the amino acid sequence of amadoriase.

Examples of amino acid substitutions yielding improved thermal stability include substitution of the amino acids at the positions corresponding to the amino acids at the positions indicated below in the amino acid sequence indicated in SEQ ID NO: 1:

(1) deletion of three amino acid residues from the carboxyl terminal, (2) substitution of alanine at position 151 with, for example, cysteine, (3) substitution of phenylalanine at position 43 with, for example, tyrosine, (4) substitution of histidine at position 53 with, for example, asparagine or tyrosine, (5) substitution of phenylalanine at position 267 with, for example, tyrosine, (6) substitution of threonine at position 350 with, for example, alanine, (7) substitution of alanine at position 185 with, for example, serine, (8) substitution of glutamic acid at position 196 with, for example, aspartic acid, (9) substitution of swine at position 299 with, for example, threonine, and

(10) substitution of valine at position 323 with, for example, glutamic acid.

A mutant of amadoriase having improved thermal stability has at least one of the aforementioned amino acid substitutions or deletions, and may have a plurality of the amino acid substitutions or deletions. For example, a mutant of amadoriase having improved thermal stability may have 1, 2, 3, 4, 5, 6, 7, 8, 9 or 10 of the aforementioned amino acid substitutions or deletions.

Among these, mutants having a substitution or deletion of an amino acid corresponding to the positions of the amino acids indicated below are preferable.

(11) A mutant having a substitution of alanine at position 151 and a substitution of serine at position 299, such as substitution of the amino acid at the position corresponding to alanine at position 151 with cysteine and substitution of the amino acid at the position corresponding to serine at position 299 with threonine.

(12) A mutant having a substitution of phenylalanine at position 43 and a substitution of alanine at position 151, such as substitution of the amino acid at the position corresponding to phenylalanine at position 43 with tyrosine and substitution of the amino acid at the position corresponding to alanine at position 151 with cysteine.

(13) A mutant having a substitution of phenylalanine at position 43 and deletion of three amino acid residues from the carboxyl terminal, such as substitution of the amino acid at the position corresponding to phenylalanine at position 43 with tyrosine and deletion of the amino acid residues at the positions corresponding to three amino acid residues from the carboxyl terminal.

(14) A mutant having a substitution of alanine at position 151, a substitution of glutamic acid at position 196 and a substitution of serine at position 299, such as substitution of the amino acid at the position corresponding to alanine at position 151 with cysteine, substitution of the amino acid at the position corresponding to glutamic acid at position 196 with aspartic acid, and substitution of the amino acid at the position corresponding to serine at position 299 with threonine.

(15) A mutant having a substitution of alanine at position 151, a substitution of serine at position 299 and deletion of three amino acid residues from the carboxyl terminal, such as substitution of the amino acid at the position corresponding to alanine at position 151 with cysteine, substitution of the amino acid at the position corresponding to serine at position 299 with threonine, and deletion of the amino acid residues at the positions corresponding to three amino acid residues from the carboxyl terminal.

(16) A mutant having a substitution of phenylalanine at position 43, a substitution of threonine at position 350 and deletion of three amino acid residues from the carboxyl terminal, such as substitution of the amino acid at the position corresponding to phenylalanine at position 43 with tyrosine, substitution of the amino acid at the position corresponding to threonine at position 350 with alanine, and deletion of the amino acid residues at the positions corresponding to three amino acid residues from the carboxyl terminal.

(17) A mutant having a substitution of phenylalanine at position 43, a substitution of alanine at position 151 and deletion of three amino acid residues from the carboxyl terminal, such as substitution of the amino acid at the position corresponding to phenylalanine at position 43 with tyrosine, substitution of the amino acid at the position corresponding to alanine at position 151 with cysteine, and deletion of the amino acid residues at the positions corresponding to three amino acid residues from the carboxyl terminal.

(18) A mutant having a substitution at phenylalanine at position 43, a substitution of alanine at position 151 and a substitution of threonine at position 350, such as substitution of the amino acid at the position corresponding to phenylalanine at position 43 with tyrosine, substitution of the amino acid at the position corresponding to alanine at position 151 with cysteine, and substitution of the amino acid at the position corresponding to threonine at position 350 with alanine.

(19) A mutant having a substitution of alanine at position 151, a substitution of glutamic acid at position 196, a substitution of serine at position 299 and a substitution of valine at position 323, such as substitution of the amino acid at the position corresponding to alanine at position 151 with cysteine, substitution of the amino acid at the position corresponding to glutamic acid at position 196 with aspartic acid, substitution of the amino acid at the position corresponding to serine at position 299 with threonine, and substitution of the amino acid at the position corresponding to valine at position 323 with glutamic acid.

(20) A mutant having a substitution of alanine at position 151, a substitution of glutamic acid at position 196, a substitution of serine at position 299 and deletion of three amino acid residues from the carboxyl terminal, such as substitution of the amino acid at the position corresponding to alanine at position 151 with cysteine, substitution of the amino acid at the position corresponding to glutamic acid at position 196 with aspartic acid, substitution of the amino acid at the position corresponding to serine at position 299 with threonine, and deletion of the amino acid residues at the positions corresponding to three amino acid residues from the carboxyl terminal.

(21) A mutant having a substitution of phenylalanine at position 43, a substitution of alanine at position 151, a substitution of threonine at position 350 and deletion of three amino acid residues from the carboxyl terminal, such as substitution of the amino acid at the position corresponding to phenylalanine at position 43 with tyrosine, substitution of the amino acid at the position corresponding to alanine at position 151 with cysteine, substitution of the amino acid at the position corresponding to threonine at position 350 with alanine, and deletion of the amino acid residues at the positions corresponding to three amino acid residues from the carboxyl terminal.

The amadoriase having superior thermal stability of the present invention includes amadoriase mutants having improved thermal stability that have a substitution that yields improvement of thermal stability as previously described in the amino acid sequence indicated in SEQ ID NO: 1, are composed of an amino acid sequence in which one or several (such as 1 to 10, preferably 1 to 5, more preferably 1 to 3, and particularly preferably 1) amino acids have been deleted, inserted, added and/or substituted at positions other than these substituted amino acids, and have amadoriase activity. Moreover, the amadoriase having superior thermal stability of the present invention also includes amadoriase mutants in which thermal stability has been modified by having an amino acid substitution mutation yielding improvement of thermal stability as previously described as well as an amino acid substitution mutation that improves properties other than thermal stability such as substrate specificity, are composed of an amino acid sequence having amino acid sequence identity of 90% or more, preferably 95% or more, more preferably 97% or more and particularly preferably 99% or more with a partial amino acid sequence from which amino acids have been removed other than the aforementioned substituted amino acids in the amino acid sequence indicated in SEQ ID NO: 1, and have amadoriase activity.

Furthermore, the amadoriase having the amino acid sequence indicated in SEQ ID NO: 1 is an amadoriase derived from *Coniochaeta* species produced by *Escherichia coli* retaining a recombinant plasmid referred to as pKK223-3-CFP-T9 in Patent Document 16, and is a modified amadoriase having superior thermal stability previously discovered by the applicant. This CFP-T9 is a quintuple mutant acquired by sequentially introducing artificial mutations at position 184, position 265, position 272, position 302 and position 388 into naturally-occurring amadoriase derived from *Coniochaeta* species.

Since CFP-T9 has extremely high heat resistance in comparison with various types of known amadoriases, the applicant considered CFP-T9 to be an example of an enzyme to serve as the basis of modification for acquiring amadoriase having even more superior heat resistance, and began a search for mutation sites using this CFP-T9. Information relating to such novel mutation sites is valuable in serving as a guide for imparting heat resistance to various types of amadoriase. Whether it be in the case of additionally introducing into a specific mutant already provided with a large number of mutations sites relating to improvement of heat resistance and the like in the manner of CFP-T9, or the case of introducing into a naturally-occurring enzyme not introduced with any special artificial mutations, an amadoriase in which thermal stability has been improved during introduction of a mutation of the present invention is included in the present invention provided heat resistance is improved in comparison with that prior to the introduction of that mutation.

In the aforementioned amino acid substitutions, although the positions of amino acids represent the positions in the amino acid sequence of amadoriase derived from *Coniochaeta* species indicated in SEQ ID NO: 1, in the amino acid sequences of amadoriases derived from other biological species, amino acids are substituted at those positions corresponding to positions in the amino acid sequence indicated in SEQ ID NO: 1. The meaning of "positions corresponding to" will be subsequently described.

(Acquisition of Gene Encoding Amadoriase)

A commonly used gene cloning method is normally used to obtain the gene of the present invention that encodes amadoriase (to be simply referred to as "amadoriase gene"). For example, chromosomal DNA or mRNA can be extracted from microbial cells or various cells having the ability to produce amadoriase using ordinary methods, such as the method described in Current Protocols in Molecular Biology (Wiley Interscience, 1989). Moreover, cDNA can also be synthesized using mRNA as a template. A chromosomal DNA or cDNA library can be produced using chromosomal DNA or cDNA obtained in this manner.

Next, DNA containing a target gene fragment that encodes amadoriase can be amplified by a method consisting of synthesizing a suitable DNA probe based on the aforementioned amino acid sequence of amadoriase and selecting an amadoriase gene from a chromosomal DNA or cDNA library using that probe, or preparing suitable primer DNA based on the aforementioned amino acid sequence and carrying out a suitable polymerase chain reaction (PCR) method such as 5'RACE or 3'RACE, followed by linking these DNA fragments to obtain DNA containing the full length of the target amadoriase gene.

Preferable examples of genes encoding amadoriase obtained in this manner include amadoriase genes derived from *Coniochaeta* species (Patent Documents 8 and 16).

Although these amadoriase genes are linked to various types of vectors in accordance with ordinary methods, they are preferable in terms of handling. An example thereof is recombinant plasmid pKK223-3-CFP (Patent Document 8), in which DNA encoding amadoriase gene derived from *Coniochaeta* sp. strain NISL 9330 is inserted into a pKK223-3 vector (Amersham Biotech).

(Vector)

Vectors able to be used in the present invention are not limited to the aforementioned plasmid, and other arbitrary vectors commonly known among persons with ordinary skill in the art can be used, examples of which include bacteriophages and cosmids. More specifically, pBluescript II SK+ (Stratagene) is preferable.

(Amadoriase Gene Mutation Treatment)

Mutation treatment can be carried out on the amadoriase gene using any known method corresponding to the intended mutated form. Namely, a wide range of methods can be used, examples of which include a method consisting of contacting a chemical serving as a mutagen to act on amadoriase gene, or recombinant DNA incorporated with that gene, and allowing it to act thereon, irradiation with ultraviolet light, genetic engineering techniques and protein engineering techniques.

Examples of chemicals serving as mutagens used in the aforementioned mutation treatment include hydroxylamine, N-methyl-N'-nitro-N-nitrosoguanidine, nitrous acid, sulfurous acid, hydrazine, formic acid and 5-bromouracil.

Conditions corresponding to the type and so forth of chemical used can be adopted for the various conditions for the aforementioned contact and action, and there are no particular limitations thereon provided a desired mutation can actually be induced in amadoriase gene. Normally, a desired mutation can be induced by allowing the aforementioned chemical to contact and act for 10 minutes or more, and preferably for 10 minutes to 180 minutes, at a reaction temperature of 20° C. to 80° C. and at a chemical concentration of preferably 0.5 M to 12 M. In the case of irradiating with ultraviolet light as well, irradiation can be carried out in accordance with ordinary methods as previously described (Chemistry Today, p. 24-30, June 1989).

A technique known as site-specific mutagenesis can typically be used as a method that utilizes protein engineering techniques. Examples thereof include the Kramer method (Nucleic Acids Res., 12, 9441 (1984); Methods Enzymol., 154, 350 (1987); Gene 37, 73 (1985)), the Eckstein method (Nucleic Acids Res., 13, 8749 (1985); Nucleic Acids Res., 13, 8765 (1985); Nucleic Acids Res., 14, 9679 (1986)), and the Kunkel method (Proc. Natl. Acad. Sci. U.S.A., 82, 488 (1985); Methods Enzymol., 154, 367 (1987)). Specific examples of methods for transforming base sequences present in DNA include methods using commercially available kits (such as the Transformer Mutagenesis Kit (Clontech), the EXOIII/Mung Bean Deletion Kit (Stratagene), and the Quick Change Site-Directed Mutagenesis Kit (Stratagene).

In addition, a technique typically known as the PCR (polymerase chain reaction) method can also be used (Technique, 1, 11 (1989)). Furthermore, in addition to the aforementioned gene modification methods, a desired modified amadoriase gene can be synthesized directly by an organic synthesis method or enzymatic synthesis method.

In the case of determining or confirming the DNA base sequence of amadoriase gene obtained according to the aforementioned methods, determination or confirmation can be carried out using, for example, the CEQ2000 Multi Capillary DNA Analysis System (Beckman Coulter).

(Transformation and Transduction)

The amadoriase gene obtained in the manner described above can be incorporated in a plasmid or other type of vector used to transform bacteriophages, cosmids, prokaryotic cells or eukaryotic cells in accordance with ordinary methods, and a host corresponding to each vector can be transformed or transduced in accordance with ordinary methods. For example, an arbitrary host such as a microorganism belonging to the genus *Escherichia*, specific examples of which include *E. coli* strain K-12, and preferably *E. coli* strain JM109 or *E. coli* strain DH5α (both available from Takara Bio), and *E. coli* strain B, and preferably *E. coli* SHuffle strain (available from New England BioLabs) or *E. coli* strain BL21 (available from Nippon Gene), can be transformed or transduced using the resulting recombinant DNA to obtain each microbial strain.

Although any arbitrary method may be used to select a strain that produces amadoriase having improved thermal stability from an acquired transformant, the following indicates an example of a method that can be used. First, several replicas are removed from LB agar medium on which the aforementioned resulting transformant has formed colonies using sterilized velvet cloth and cultured on fresh agar medium. Once the colonies on the agar medium to which the replicas have been transferred reach sufficient size, a film impregnated with a lysing agent such as lysozyme is placed over the medium followed by allowing to stand undisturbed for 1 hour at 37° C. to lyse the cells. At this time, a crude enzyme liquid obtained by lysing the cells adheres to the film.

After allowing the film adhered with crude enzyme liquid as described above to stand undisturbed for 30 minutes under temperature conditions such as a temperature of 55° C. suitable for evaluating thermal stability, the film is laminated with a film immersed in a substrate in the form of 0.1 M potassium phosphate buffer (pH 7.0) containing fructosyl valine, peroxidase, TOOS and 4-aminoantipyrine followed by observation of the degree of the development of a violet color. A coloring test is also carried out using the same procedure on an amadoriase-producing strain prior to modification, and a target transformant is selected based on a comparison therewith. The degree of coloring of colonies of an amadoriase-producing strain prior to modification can be lowered by carrying out heat treatment by selecting temperature conditions such that the amadoriase prior to modification undergoes a considerable loss of activity. By then selecting those colonies exhibiting a high degree of coloring by comparing therewith, colonies can be selected that produce modified amadoriase having improved thermal stability.

Mutant amadoriase having even more superior thermal stability, and a transformant having the ability to produce that amadoriase, can also be obtained by further repeating introduction of mutations according to the aforementioned modification method using a transformant that produces amadoriase having improved thermal stability obtained in the manner described above.

Examples of transformants that produce amadoriase having superior thermal stability obtained in the manner described above include microorganisms producing amadoriase having improved residual activity (%) following heat treatment for 30 minutes at 55° C. or for 30 minutes at 60° C. at pH 7.0 such as *E. coli* SHuffle strain (pKK223-3-CFP-T11), *E. coli* SHuffle strain (pKK223-3-CFP-T12), *E. coli* SHuffle strain (pKK223-3-CFP-T13), *E. coli* SHuffle strain (pKK223-3-CFP-T14), *E. coli* SHuffle strain (pKK223-3-CFP-T15), *E. coli* SHuffle strain (pKK223-3-CFP-T16), *E. coli* SHuffle strain (pKK223-3-CFP-T17), *E. coli* SHuffle strain (pKK223-3-CFP-T18), *E. coli* SHuffle strain (pKK223-3-CFP-T19), *E. coli* SHuffle strain (pKK223-3-CFP-T20), *E. coli* SHuffle strain (pKK223-3-CFP-T21), *E. coli* SHuffle strain (pKK223-3-CFP-T22), *E. coli* SHuffle strain (pKK223-3-CFP-T23), *E. coli* SHuffle strain (pKK223-3-CFP-T24), *E. coli* SHuffle strain (pKK223-3-CFP-T25), *E. coli* SHuffle strain (pKK223-3-CFP-T26), *E. coli* SHuffle strain (pKK223-3-CFP-T27), *E. coli* SHuffle strain (pKK223-3-CFP-T28), *E. coli* SHuffle strain (pKK223-3-CFP-T29), *E. coli* SHuffle strain (pKK223-3-CFP-T30), *E. coli* SHuffle strain (pKK223-3-CFP-T31) or *E. coli* SHuffle strain (pKK223-3-CFP-T32).

(Amino Acid Sequence Homology)

Sequence homology of an amino acid sequence can be calculated with a program such as the maximum matching or search homology program of Genetyx-Mac (Software Development) or by a program such as the maximum matching or multiple alignment program of DNASIS Pro (Hitachi Software).

(Specification of Positions Corresponding to Amino Acids)

A "position corresponding to an amino acid" refers to a position in an amino acid sequence of amadoriase derived from another biological species corresponding to an amino acid at a specific position of the amino acid sequence of amadoriase derived from *Coniochaeta* species indicated in SEQ ID NO: 1.

An example of a method for specifying a "position corresponding to an amino acid" can be carried out by comparing amino acid sequences using a known algorithm such as the Lipman-Pearson algorithm, and imparting maximum homology to retained amino acid residues present in the amino acid sequence of each amadoriase. By aligning amino acid sequences of amadoriases using this type of method, the positions of homologous amino acid residues in the sequence of each amadoriase sequence can be determined irrespective of insertions or deletions in the amino acid sequence. Since homologous positions are thought to be present at the same positions in a three-dimensional structure, they can be assumed to have similar effects with respect to substrate specificity of a target amadoriase.

FIG. 1 indicates examples of amadoriase sequences derived from various known biological species. The amino acid sequence indicated by SEQ ID NO: 1 is shown in the uppermost row. Each of the sequences shown in FIG. 1 has homology of 75% or more with the sequence of SEQ ID NO: 1 and has been arranged using a known algorithm. The drawing indicates mutation sites in mutations of the present invention. The positions of amino acids in the amino acid sequences of amadoriases derived from other biological species that correspond to amino acids at specific positions in the amino acid sequence of amadoriase derived from *Coniochaeta* species can be determined from FIG. 1. FIG. 1 shows the amino acid sequences of *Coniochaeta* species-derived amadoriase (SEQ ID NO: 1), *Eupenicillium* terrenum-derived amadoriase (SEQ ID NO: 16), *Pyrenochaeta* species-derived ketoamine oxidase (SEQ ID NO: 26), *Arthrinium* species-derived ketoamine oxidase (SEQ ID NO: 27), *Curvularia clavata*-derived ketoamine oxidase (SEQ ID NO: 28), *Neocosmospora* vasinfecta-derived ketoamine oxidase (SEQ ID NO: 29), *Cryptococcus neoformans*-derived fructosyl amino acid oxidase (SEQ ID NO: 30), *Phaeosphaeria nodorum*-derived fructosyl peptide oxidase (SEQ ID NO: 20), *Aspergillus nidulans*-derived fructosyl amino acid oxidase (SEQ ID NO: 31), *Ulocladium* species-derived fructosyl amino acid oxidase (SEQ ID NO: 32) and *Penicillium crysogenum*-derived fructosyl amino acid oxidase (SEQ ID NO: 33).

(Positions Corresponding to Substitution Sites)

Furthermore, in the present invention, "the position corresponding to phenylalanine at position 43 of the amino acid sequence described in SEQ ID NO: 1" refers to an amino acid corresponding to phenylalanine at position 43 of the amadoriase of SEQ ID NO: 1 in the case of having compared a determined amino acid sequence of amadoriase with the amino acid sequence of amadoriase derived from *Coniochaeta* species indicated in SEQ ID NO: 1. As a result, this position can be specified according to FIG. 1 in which amino acid sequences have been aligned using the aforementioned method for specifying an "amino acid residue of a corresponding position".

Namely, this refers to tyrosine at position 43 in the amadoriase derived from *Eupenicillium terrenum*, tyrosine at position 43 in the ketoamine oxidase derived from *Pyrenochaeta* species, tyrosine at position 43 in the ketoamine oxidase derived from *Arthrinium* species, tyrosine at position 43 in the ketoamine oxidase derived from *Curvularia clavata*, tyrosine at position 43 in the ketoamine oxidase derived from *Neocosmospora vasinfecta*, tyrosine at position 43 in the fructosyl amino acid oxidase derived from *Cryptococcus neoformans*, tyrosine at position 43 in the fructosyl peptide oxidase derived from *Phaeosphaeria nodorum*, cysteine at position 42 in the fructosyl amino acid oxidase derived from *Aspergillus nidulans*, tyrosine at position 43 in the fructosyl amino acid oxidase derived from *Ulocladium* species, and tyrosine at position 43 in the fructosyl amino acid oxidase derived from *Penicillium crysogenum*.

In addition, "the position corresponding to histidine at position 53 of the amadoriase described in SEQ ID NO: 1" refers to an amino acid corresponding to histidine at position 53 of the amino acid sequence described in SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to histidine at position 53 in the amadoriase derived from *Eupenicillium terrenum*, asparagine at position 53 in the ketoamine oxidase derived from *Pyrenochaeta* species, asparagine at position 53 in the ketoamine oxidase derived from *Arthrinium* species, asparagine at position 53 in the ketoamine oxidase derived from *Curvularia clavata*, asparagine at position 53 in the ketoamine oxidase derived from *Neocosmospora vasinfecta*, asparagine at position 53 in the fructosyl amino acid oxidase derived from *Cryptococcus neoformans*, asparagine at position 53 in the fructosyl peptide oxidase derived from *Phaeosphaeria nodorum*, tyrosine at position 52 in the fructosyl amino acid oxidase derived from *Aspergillus nidulans*, asparagine at position 53 in the fructosyl amino acid oxidase derived from *Ulocladium* species, and tyrosine at position 53 in the fructosyl amino acid oxidase derived from *Penicillium crysogenum*.

In addition, "the position corresponding to alanine at position 151 of the amino acid sequence described in SEQ ID NO: 1" refers to an amino acid corresponding to alanine at position 151 of the amadoriase of SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to glycine at position 151 in the amadoriase derived from *Eupenicillium terrenum*, alanine at position 151 in the ketoamine oxidase derived from *Pyrenochaeta* species, alanine at position 151 in the ketoamine oxidase derived from *Arthrinium* species, alanine at position 151 in the ketoamine oxidase derived from *Curvularia clavata*, alanine at position 151 in the ketoamine oxidase derived from *Neocosmospora vasinfecta*, alanine at position 151 in the fructosyl amino acid oxidase derived from *Cryptococcus neoformans*, alanine at position 149 in the fructosyl peptide oxidase derived from *Phaeosphaeria nodorum*, glycine at position 150 in the fructosyl amino acid oxidase derived from *Aspergillus nidulans*, alanine at position 151 in the fructosyl amino acid oxidase derived from *Ulocladium* species, and glycine at position 151 in the fructosyl amino acid oxidase derived from *Penicillium crysogenum*.

In addition, "the position corresponding to alanine at position 185 of the amadoriase described in SEQ ID NO: 1" refers to an amino acid corresponding to alanine at position 185 of the amino acid sequence described in SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to alanine at position 185 in the amadoriase derived from *Eupenicillium terrenum*, alanine at position 185 in the ketoamine oxidase derived from *Pyrenochaeta* species, alanine at position 185 in the ketoamine oxidase derived from *Arthrinium* species, alanine at position 185 in the ketoamine oxidase derived from *Curvularia clavata*, alanine at position 185 in the ketoamine oxidase derived from *Neocosmospora vasinfecta*, alanine at position 185 in the fructosyl amino acid oxidase derived from *Cryptococcus neoformans*, alanine at position 183 in the fructosyl peptide oxidase derived from *Phaeosphaeria nodorum*, alanine at position 184 in the fructosyl amino acid oxidase derived from *Aspergillus nidulans*, alanine at position 185 in the fructosyl amino acid oxidase derived from *Ulocladium* species, and alanine at position 185 in the fructosyl amino acid oxidase derived from *Penicillium crysogenum*.

In addition, "the position corresponding to glutamic acid at position 196 of the amadoriase described in SEQ ID NO: 1" refers to an amino acid corresponding to glutamic acid at position 196 of the amino acid sequence described in SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to aspartic acid at position 196 in the amadoriase derived from *Eupenicillium terrenum*, glycine at position 196 in the ketoamine oxidase derived from *Pyrenochaeta* species, aspartic acid at position 196 in the ketoamine oxidase derived from *Arthrinium* species, glycine at position 196 in the ketoamine oxidase derived from *Curvularia clavata*, aspartic acid at position 196 in the ketoamine oxidase derived from *Neocosmospora vasinfecta*, aspartic acid at position 196 in the fructosyl amino acid oxidase derived from *Cryptococcus neoformans*, glycine at position 194 in the fructosyl peptide oxidase derived from *Phaeosphaeria nodorum*, alanine at position 195 in the fructosyl amino acid oxidase derived from *Aspergillus nidulans*, glycine at position 196 in the fructosyl amino acid oxidase derived from *Ulocladium* species, and aspartic acid at position 196 in the fructosyl amino acid oxidase derived from *Penicillium crysogenum*.

Moreover, "the position corresponding to phenylalanine at position 267 of the amino acid sequence described in SEQ ID NO: 1" refers to an amino acid corresponding to phenylalanine at position 267 of the amadoriase of SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to phenylalanine at position 267 in the amadoriase derived from *Eupenicillium terrenum*, phenylalanine at position 265 in the ketoamine oxidase derived from *Pyrenochaeta* species, phenylalanine at position 267 in the ketoamine oxidase derived from *Arthrinium* species, phenylalanine at position 265 in the ketoamine oxidase derived from *Curvularia clavata*, phenylalanine at position 267 in the ketoamine oxidase derived from *Neocosmospora vasinfecta*, phenylalanine at position 267 in the fructosyl amino acid oxidase derived from *Cryptococcus neoformans*, phenylalanine at position 263 in the fructosyl peptide oxidase derived from *Phaeosphaeria nodorum*, phenylalanine at position 267 in the fructosyl amino acid oxidase derived from *Aspergillus nidulans*, phenylalanine at position 265 in the fructosyl amino acid oxidase derived from *Ulocladium* species, and phenylalanine at position 267 in the fructosyl amino acid oxidase derived from *Penicillium crysogenum*.

Moreover, "the position corresponding to serine at position 299 of the amino acid sequence described in SEQ ID NO: 1" refers to an amino acid corresponding to serine at position 299 of the amadoriase of SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to serine at position 299 in the amadoriase derived from *Eupenicillium terrenum*, alanine at position 297 in the ketoamine oxidase derived from *Pyrenochaeta* species, alanine at position 300 in the ketoamine oxidase derived from *Arthrinium* species, alanine at position 297 in the ketoamine oxidase derived from *Curvularia clavata*, alanine at position 299 in the ketoamine oxidase derived from *Neocosmospora vasinfecta*, serine at position 299 in the fructosyl amino acid oxidase derived from *Cryptococcus neoformans*, alanine at position 295 in the fructosyl peptide oxidase derived from *Phaeosphaeria*

*nodorum*, alanine at position 299 in the fructosyl amino acid oxidase derived from *Aspergillus nidulans*, alanine at position 297 in the fructosyl amino acid oxidase derived from *Ulocladium* species, and serine at position 299 in the fructosyl amino acid oxidase derived from *Penicillium crysogenum*.

Moreover, "the position corresponding to valine at position 323 of the amino acid sequence described in SEQ ID NO: 1" refers to an amino acid corresponding to valine at position 323 of the amadoriase of SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to valine at position 323 in the amadoriase derived from *Eupenicillium terrenum*, alanine at position 321 in the ketoamine oxidase derived from *Pyrenochaeta* species, glutamine at position 324 in the ketoamine oxidase derived from *Arthrinium* species, lysine at position 321 in the ketoamine oxidase derived from *Curvularia clavata*, glutamic acid at position 323 in the ketoamine oxidase derived from *Neocosmospora vasinfecta*, alanine at position 323 in the fructosyl amino acid oxidase derived from *Cryptococcus neoformans*, valine at position 319 in the fructosyl peptide oxidase derived from *Phaeosphaeria nodorum*, valine at position 323 in the fructosyl amino acid oxidase derived from *Aspergillus nidulans*, valine at position 321 in the fructosyl amino acid oxidase derived from *Ulocladium* species, and glutamic acid at position 323 in the fructosyl amino acid oxidase derived from *Penicillium crysogenum*.

Moreover, "the position corresponding to threonine at position 350 of the amino acid sequence described in SEQ ID NO: 1" refers to an amino acid corresponding to threonine at position 350 of the amadoriase of SEQ ID NO: 1 in the case of having compared a determined amino acid sequence of amadoriase with the amino acid sequence of amadoriase derived from *Coniochaeta* species indicated in SEQ ID NO: 1. This position can also be specified according to FIG. 1 in which amino acid sequences have been aligned using the aforementioned method.

Namely, this refers to threonine at position 350 in the amadoriase derived from *Eupenicillium terrenum*, threonine at position 348 in the ketoamine oxidase derived from *Pyrenochaeta* species, threonine at position 351 in the ketoamine oxidase derived from *Arthrinium* species, threonine at position 348 in the ketoamine oxidase derived from *Curvularia clavata*, threonine at position 350 in the ketoamine oxidase derived from *Neocosmospora vasinfecta*, threonine at position 350 in the fructosyl amino acid oxidase derived from *Cryptococcus neoformans*, threonine at position 346 in the fructosyl peptide oxidase derived from *Phaeosphaeria nodorum*, threonine at position 350 in the fructosyl amino acid oxidase derived from *Aspergillus nidulans*, threonine at position 348 in the fructosyl amino acid oxidase derived from *Ulocladium* species, and threonine at position 350 in the fructosyl amino acid oxidase derived from *Penicillium crysogenum*.

(Positions Corresponding to Carboxyl Terminal Deletion Sites)

The "positions corresponding to three amino acid residues from the carboxyl terminal of the amadoriase described in SEQ ID NO: 1" refer to three amino acid residues from the carboxyl terminal of the amino acid sequence described in SEQ ID NO: 1 in the case of having compared a determined amino acid sequence of amadoriase with the amino acid sequence of amadoriase derived from *Coniochaeta* species indicated in SEQ ID NO: 1. The sequence of three residues at these positions in amadoriase derived from *Coniochaeta* species is composed of proline at position 465, lysine at position 436 and leucine at position 437, and a sequence of amino acids at positions corresponding thereto can also be specified according to FIG. 1 in which amino acid sequences have been aligned using the aforementioned method.

Namely, the three amino acids of the carboxyl terminal are composed of alanine at position 435, histidine at position 436 and leucine at position 437 in the amadoriase derived from *Eupenicillium terrenum*, the three amino acids of the carboxyl terminal are composed of alanine at position 438, lysine at position 439 and leucine at position 440 in the ketoamine oxidase derived from *Pyrenochaeta* species, the three amino acids of the carboxyl terminal are composed of histidine at position 450, lysine at position 451 and leucine at position 452 in the ketoamine oxidase derived from *Arthrinium* species, the three amino acids of the carboxyl terminal are composed of serine at position 438, lysine at position 439 and leucine at position 440 in the ketoamine oxidase derived from *Curvularia clavata*, the three amino acids of the carboxyl terminal are composed of alanine at position 435, asparagine at position 436 and leucine at position 437 in the fructosyl peptide oxidase derived from *Phaeosphaeria nodorum*, the three amino acids of the carboxyl terminal are composed of alanine at position 436, lysine at position 437 and methionine at position 438 in the fructosyl amino acid oxidase derived from *Aspergillus nidulans*, the three amino acids of the carboxyl terminal are composed of alanine at position 439, lysine at position 440 and leucine at position 441 in the fructosyl amino acid oxidase derived from *Ulocladium* species, and the three amino acids of the carboxyl terminal are composed of alanine at position 435, lysine at position 436 and leucine at position 437 in the fructosyl amino acid oxidase derived from *Penicillium crysogenum*.

Furthermore, a motif in the form of peroxisome targeting signal 1 (PTS1), which functions as a signal sequence for transporting protein to peroxisomes and is composed of three amino acids from the carboxyl terminal, is known to be present in eukaryotes. A well-known example of a PTS1 motif is a motif composed of the sequence consisting of (proline/serine/alanine/cysteine)-(lysine/histidine/arginine/asparagine)-(leucine/methionine) (see, for example, FEBS J., 272, 2362 (2005); Plant Cell Physiol., 38, 759 (1997); or Eur. J. Cell Biol., 71, 248 (1996)). Although yet to be verified in detail, the possibility can be suggested on the basis of this finding that the region of "positions corresponding to three amino acid residues from the carboxyl terminal of the amino acid sequence described in SEQ ID NO: 1", which is one of the mutated sites of the present invention that contributes to improved thermal stability, is equivalent to a so-called PTS1 motif in amadoriase.

(Production of Amadoriase of Present Invention)

In order to produce amadoriase having superior thermal stability obtained in the manner described above using a microbial strain having the ability to produce that amadoriase, although the microbial strain may be cultured by an ordinary solid culturing method, the microbial strain is preferably cultured using a liquid culturing method whenever possible.

In addition, a medium obtained by adding one or more types of inorganic salts, such as sodium chloride, monopotassium phosphate, dipotassium phosphate, magnesium sulfate, magnesium chloride, ferric chloride, ferric sulfate or manganese sulfate, to one or more types of nitrogen sources, such as yeast extract, tryptone, peptone, beef extract, corn stiplica or soybean or wheat bran, and suitably adding a sugar raw material or vitamins and the like as necessary, is used for the medium used to culture the aforementioned microbial strain.

Furthermore, the initial pH of the medium is suitably adjusted to pH 7 to 9.

In addition, although culturing can be carried out using arbitrary conditions, culturing can be carried out by, for example, aeration-agitation submerged culturing, shake culturing or static culturing for 4 hours to 24 hours at a culturing temperature of 20° C. to 42° C., and preferably about 37° C., and more preferably culturing for 4 hours to 8 hours at a culturing temperature of about 37° C.

Following completion of culturing, an ordinary enzyme collection means can be used to collect amadoriase from the culture. For example, amadoriase can be collected by subjecting microbial cells to ultrasonic crushing or pulverization or using a lytic enzyme such as lysozyme to extract the enzyme, or the microbial cells can be lysed by shaking or allowing to stand in the presence of toluene and the like to discharge the enzyme outside the cells. After removing solid components by subjecting the solution to filtering or centrifugal separation and the like, and further removing nucleic acids as necessary using streptomycin hydrochloride, protamine sulfate or manganese sulfate, fractionation is carried out by adding ammonium sulfate, alcohol or acetone and the like thereto followed by collecting the precipitate to obtain crude amadoriase.

(Improvement of Thermal Stability of Amadoriase of Present Invention)

The amadoriase of the present invention obtained using means as described above is characterized by demonstrating improved thermal stability in comparison with that prior to modification as a result of inducing a mutation in the amino acid sequence thereof by genetic modification and the like. More specifically, in comparison with that prior to modification, the amadoriase of the present invention is characterized by demonstrating improved residual activity (%) following a prescribed treatment, such as following heat treatment for 30 minutes at 55° C. or for 30 minutes at 60° C., under the reaction conditions described in the activity measurement method and thermal stability evaluation method described in the present description, in comparison with that prior to introduction of a mutation of the present invention.

Although there are no particular limitations on the degree of improvement of residual activity (%), amadoriase is included in the present invention in which, for example, residual activity improves by 3% or more, preferably 10% or more, more preferably 20% or more, even more preferably 30% or more and most preferably 40% or more in a comparison of values of residual activity (%) before and after introduction of a mutation of the present invention. Alternatively, amadoriase is included in the present invention in which a value (residual activity ratio) obtained by dividing residual activity (%) after introducing a mutation of the present invention by residual activity (%) prior to introduction of a mutation of the present invention is greater than 1, preferably 5 or more, more preferably 10 or more and even more preferably 50 or more.

In actuality, since relative evaluation results also differ according to the degree of thermal stability of the amadoriase prior to introduction of a mutation in addition to the temperature conditions at the time of measurement, it is difficult to evaluate the absolute thermal stability of each mutant by only comparing the magnitudes of residual activity (%) or residual activity ratio. The degree of improvement of residual activity (%) and residual activity ratio tend to be calculated on the high side by selecting heating conditions at which the residual activity (%) of amadoriase prior to introduction of a mutation is calculated to be sufficiently low with the intent of facilitating selection of the amadoriase of the present invention.

For example, when amadoriases of the present invention produced by E. coli SHuffle strain (pKK223-3-CFP-T11), E. coli SHuffle strain (pKK223-3-CFP-T12), E. coli SHuffle strain (pKK223-3-CFP-T13), E. coli SHuffle strain (pKK223-3-CFP-T14), E. coli SHuffle strain (pKK223-3-CFP-T15), E. coli SHuffle strain (pKK223-3-CFP-T16), E. coli SHuffle strain (pKK223-3-CFP-T17), E. coli SHuffle strain (pKK223-3-CFP-T18), E. coli SHuffle strain (pKK223-3-CFP-T19), E. coli SHuffle strain (pKK223-3-CFP-T20) and E. coli SHuffle strain (pKK223-3-CFP-T21), which are included in the present invention, are subjected to heat treatment for 50 minutes at 55° C. and pH 7.0, in contrast to residual activity of amadoriase prior to introduction of a mutation of the present invention in the form of CFP-T9 being about 53%, the amadoriases of the present invention demonstrate residual activity in excess of 55%, in excess of 60% among those exhibiting high levels of residual activity, and in excess of 80% among those exhibiting even higher levels of residual activity. In addition, when the amadoriases of the present invention produced by E. coli SHuffle strain (pKK223-3-CFP-T22), E. coli SHuffle strain (pKK223-3-CFP-T23), E. coli SHuffle strain (pKK223-3-CFP-T24), E. coli SHuffle strain (pKK223-3-CFP-T25), E. coli SHuffle strain (pKK223-3-CFP-T26), E. coli SHuffle strain (pKK223-3-CFP-T27), E. coli SHuffle strain (pKK223-3-CFP-T28), E. coli SHuffle strain (pKK223-3-CFP-T29), E. coli SHuffle strain (pKK223-3-CFP-T30), E. coli SHuffle strain (pKK223-3-CFP-T31) and E. coli SHuffle strain (pKK223-3-CFP-T32) are subjected to heat treatment for 30 minutes at 60° C. and pH 7.0, in contrast to residual activity of amadoriase prior to introduction of a mutation of the present invention in the form of CFP-T9 being about 0.34%, the amadoriases of the present invention demonstrate residual activity in excess of 2%, in excess of 20% among those exhibiting high levels of residual activity, in excess of 30% among those exhibiting even higher levels of residual activity, in excess of 40% among those exhibiting even higher levels of residual activity, in excess of 50% among these exhibiting still higher levels of residual activity, and in excess of 60% among those exhibiting even higher levels of residual activity. Amadoriase having improved thermal stability in this manner demonstrates remarkably improved storage stability in products containing that enzyme, and is also stable in cases of being subjected to heat in a manufacturing process, thereby making this extremely industrially useful.

(Measurement of Amadoriase Activity)

Although various methods can be used to measure the activity of amadoriase, as an example thereof, the following provides an explanation of the method used to measure amadoriase activity used in the present invention.

(Measurement of Amadoriase Activity)

Examples of methods mainly used to measure the enzyme activity of amadoriase in the present invention include a method that measures the amount of hydrogen peroxide formed by an enzyme reaction, and a method that measures the amount of oxygen consumed by an enzyme reaction. The following indicates an example of a method that measures the amount of hydrogen peroxide.

Fructosyl valine is used as substrate in the following measurement of amadoriase activity in the present invention unless specifically indicated otherwise. Furthermore, enzyme titer is such that 1 U is defined as the amount of enzyme that forms 1 μmol of hydrogen peroxide in 1 minute when measured using fructosyl valine as substrate.

Glycated amino acids such as fructosyl valine and glycated peptides such as fructosyl valyl histidine can be synthesized and purified based on the method of Sakagami, et al (see Patent Document 3).

A. Preparation of Reagents (1) Reagent 1: POD-4-AA Solution 4.0 kU of peroxidase (Kikkoman) and 100 mg of 4-aminoantipyrine (Tokyo Chemical Industry) are dissolved in 0.1 M potassium phosphate buffer (pH 7.0) and brought to a final volume of 1 L.

(2) Reagent 2: TOOS Solution 500 mg of TOOS (Dojindo Laboratories) are dissolved in ion exchange water and brought to a final volume of 100 ml.

(3) Reagent 3: Substrate Solution (150 mM, Final Concentration: 5 mM)

417 mg of fructosyl valine are dissolved in ion exchange water and brought to a final volume of 10 ml.

B. Measurement Method 2.7 ml of Reagent 1, 100 μl of Reagent 2 and 100 μl of enzyme liquid are mixed followed by preliminarily warming for 5 minutes at 37° C. Subsequently, 100 μl of Reagent 3 are added and mixed followed by measuring absorbance at 555 nm with a spectrophotometer (U-3010, Hitachi High Technologies). The change in absorbance at 555 nm per minute from 1 minute to 3 minutes is used for the measured value. Furthermore, a control liquid is prepared in the same manner with the exception of adding 100 μl of ion exchange water instead of 100 μl of Reagent 3. The number of micromoles of hydrogen peroxide formed per minute at 37° C. is defined as the activity unit (U) in the enzyme liquid, and is calculated according to the equation indicated below.

$$\text{Activity (U/ml)} = \{(\Delta As - \Delta A_0) \times 3.0 \times df\} \div (39.2 \times 0.5 \times 0.1)$$

$\Delta As$: Change in absorbance per minute of reaction liquid $\Delta A_0$: Change in absorbance per minute of control liquid 39.2: Millimolar absorption coefficient of quinone imine pigment formed by reaction ($mM^{-1}$, $cm^{-1}$)

0.5: Number of moles of quinone imine pigment formed by 1 mole of hydrogen peroxide df: Dilution factor (Measurement of Thermal Stability)

Crude amadoriase or purified amadoriase is diluted with 0.1 M phosphate buffer (pH 7.0) containing 10% xylitol to a concentration of about 0.5 U/ml followed by warming for 30 minutes at 55° C. Enzyme activity of the sample before and after heating is measured using the method previously described in Section B, and thermal stability is evaluated by determining the ratio of activity after heating in the case of assigning a value of 100 to the activity before heating, namely residual activity (%).

The following provides a more detailed explanation of the present invention according to examples thereof. However, the technical scope of the present invention is not limited to these examples.

Example 1

(1) Preparation of Recombinant Plasmid pKK223-3-CFP-T9 DNA

E. coli strain JM109 having a recombinant plasmid containing CFP-T9 gene (SEQ ID NO: 2) (pKK223-3-CFP-T9) (see Patent Document 16) was inoculated into 100 ml of LB-amp medium (1% (w/v) Bacto Tryptone, 0.5% (w/v) peptone, 0.5% (w/v) NaCl, 50 μg/ml ampicillin) followed by culturing for 20 hours at 37° C. to obtain a culture.

This culture was centrifuged for 5 minutes at 7,000 rpm to collect the microorganisms and obtain microbial cells. Next, recombinant plasmid pKK223-3-CFP-T9 was extracted from the cells using Qiagen-tip 100 (Qiagen) and then purified to obtain 100 μg of recombinant plasmid pKK223-3-CFP-T9.

(2) Recombinant Plasmid pKK223-3-CFP-T9 DNA Modification Procedure

E. coli XL1-Red (Stratagene) competent cells (which are easily modified by being susceptible to the occurrence of errors in plasmid replication during cell proliferation) were transformed in accordance with the method of D. M. Morrison (Methods in Enzymology, 68, 326-331, 1979) using 20 μg of the 100 μg of the aforementioned recombinant plasmid pKK223-3-CFP-T9 DNA to obtain about 15,000 strains of transformants.

In order to recover plasmid DNA from all colonies of the aforementioned transformants, a suitable amount of Qiagen Sol I (Qiagen) was added to the agar medium on which the aforementioned recombinants were grown, the colonies were scraped together along with the Qiagen Sol I using a spreader, the solution was recovered with a Pipetman, and plasmid recovery was subsequently carried out in accordance with an established method to obtain 100 μg of modified recombinant plasmid pKK223-3-CFP-T9 DNA. E. coli strain JM109 was transformed in accordance with the method of D. M. Morrison (Methods in Enzymology, 68, 326-331, 1979) using 20 μg of that plasmid pKK223-3-CFP-T9 DNA to obtain about 3,000 strains of transformants retaining modified plasmids.

(3) Determination of Amadoriase Having Superior Thermal Stability

First, all of the aforementioned resulting transformants were replicated on fresh LB-amp agar medium using velvet cloth. Colonies on the replica plate were transferred to Hybond-N+ (Amersham) and immersed in BugBuster Protein Extraction Reagent (Novagen). After treating this Hybond-N+ for 1 hour at 55° C., immersion in 0.1 M potassium phosphate buffer (pH 7.0) containing 2 mM fructosyl valine, 4 U/ml peroxidase (Kikkoman), 1 mg/ml 4-aminoantipyrine (Tokyo Chemical Industry) and 10 mg/ml TOOS (Dojin Laboratories) resulted in the observation of a small number of strains exhibiting strong coloring.

Colonies corresponding to this strong coloring were selected from a master plate and liquid-cultured in 2 ml of LB-amp medium to induce production of plasmid-encoded modified amadoriase.

Following culturing, the resulting cells were respectively washed with 0.1 M potassium phosphate buffer (pH 8.0), subjected to ultrasonic crushing, and centrifuged for 10 minutes at 15,000 rpm to prepare 1.5 ml aliquots of their respective crude enzyme liquids. These crude enzyme liquids were then used to calculate residual activity (%) of the modified amadoriase (activity after treatment/activity before treatment) in accordance with the method previously described in the section on Measurement of Thermal Stability.

On the other hand, E. coli strain JM109 (pKK223-3-CFP-T9) producing amadoriase (CFP-T9) prior to modification was cultured in the same manner and subjected to extraction, heat treatment and measurement of activity followed by calculation of residual activity (%), and 8 types of modified amadoriase having improved residual activity ratios, along with the *E. coli* in which they are produced, were able to be obtained.

The resulting 8 strains were shake-cultured for 18 hours at 37° C. in 2 ml of LB-amp medium and plasmids were isolated from the culture liquid using Qiagen-tip 100 (Qiagen). The plasmids were respectively named pKK223-3-CFP-T11, pKK223-3-CFP-T12, pKK223-3-CFP-T13, pKK223-3-CFP-T14, pKK223-3-CFP-T15, pKK223-3-CFP-T17, pKK223-3-CFP-T18 and pKK223-3-CFP-T19, and the base sequence of DNA encoding amadoriase in each plasmid was determined using the CEQ2000 Multi-Capillary DNA Analysis System (Beckman Coulter).

As a result, a mutation that substitutes glutamic acid at position 196 in the amino acid sequence of SEQ ID NO: 1 with aspartic acid was determined to be introduced in pKK223-3-CFP-T11, a mutation that substitutes serine at position 299 in the amino acid sequence of SEQ ID NO: 1 with threonine was determined to be introduced in pKK223-3-CFP-T12, a mutation that substitutes valine at position 323 in the amino acid sequence of SEQ ID NO: 1 with glutamic acid was determined to be introduced in pKK223-3-CFP-T13, a mutation that substitutes phenylalanine at position 43 in the amino acid sequence of SEQ ID NO: 1 with tyrosine was determined to be introduced in pKK223-3-CFP-T14, a mutation that substitutes histidine at position 53 in the amino acid sequence of SEQ ID NO: 1 with asparagine was determined to be introduced in pKK223-3-CFP-T15, a mutation that substitutes alanine at position 185 in the amino acid sequence of SEQ ID NO: 1 with serine was determined to be introduced in pKK223-3-CFP-T17, a mutation that substitutes phenylalanine at position 267 in the amino acid sequence of SEQ ID NO: 1 with tyrosine was determined to be introduced in pKK223-3-CFP-T18, and a mutation that substitutes threonine at position 350 in the amino acid sequence of SEQ ID NO: 1 with alanine was determined to be introduced in pKK223-3-CFP-T19.

(Point Mutation Test of Histidine at Position 53)

Patent Document 17 indicates that heat resistance improves when tyrosine at position 52 in fructosyl amino acid oxidase derived from *Aspergillus nidulans*, which corresponds to histidine at position 53 of the amino acid sequence described in SEQ ID NO: 1, is substituted with histidine. Therefore, in order to verify whether or not the same effect is present in CFP-T9, amadoriase was attempted to be produced in which histidine at position 53 of the amino acid sequence described in SEQ ID NO: 1 is substituted with tyrosine. Using recombinant plasmid pKK223-3-CFP-T9 DNA as template, the primers composed of the DNA sequences of SEQ ID NO: 3 and SEQ ID NO: 4 were synthesized in accordance with ordinary methods with the intent of substituting histidine at position 53 of CFP-T9 with tyrosine. Next, using the aforementioned resulting recombinant plasmid pKK223-3-CFP-T9 DNA as template, a PCR reaction was carried out under the conditions indicated below using the primers of SEQ ID NO: 3 and SEQ ID NO: 4 and KOD-Plus-(Toyobo).

Namely, 5 μl of 10×KOD-Plus-buffer, 5 μl of a mixed solution of dNTPs prepared so that the concentration of each dNTP was 2 mM, 2 μl of 25 mM $MgSO_4$ solution, 50 ng of pKK223-3-CFP-T9 DNA serving as template, 15 pmol of each of the aforementioned synthetic oligonucleotides and 1 unit of KOD-Plus- were added followed by bringing to a total volume of 50 μl with sterile water. The prepared reaction liquid was incubated for 2 minutes at 94° C. followed by repeating 30 cycles consisting of 15 seconds at 94° C., 30 seconds at 50° C. and 6 minutes at 68° C. using a thermal cycler (Eppendorf).

A portion of the reaction liquid was electrophoresed in 1.0% agarose gel to confirm that DNA of approximately 6,000 bp is specifically amplified. The resulting DNA was treated using restrictase DpnI (New England Biolabs) followed by cleaving the remaining template DNA, transforming *E. coli* strain JM109 and applying to LB-amp agar medium. The colonies that formed were inoculated into LB-amp medium followed by shake culturing and isolating the plasmid DNA using the same method as that described in (1) above. The base sequence of DNA that encodes amadoriase in the plasmid was determined using the CEQ2000 Multi Capillary DNA Analysis System (Beckman Coulter), and a recombinant plasmid (pKK233-3-CFP-T16) was obtained that encodes a modified amadoriase in which histidine at position 53 of the amino acid sequence described in SEQ ID NO: 1 is substituted with tyrosine.

(4) Modification of pKK233-3-CFP-T9 DNA Based on Known Enzyme Structural Data (Modification for Producing Intramolecular Crosslinking)

A technique consisting of inducing the formation of new disulfide bonds within a protein molecule is also known to be a method for improving the thermal stability of a protein (see, for example, Science, 226, 555-557, 1984). Therefore, an attempt was made to predict the three-dimensional structure of CFP-T9 by referring to the three-dimensional structure of Amadoriase II (see, for example, Jr. Biol. Chem., 283, 27007-27016, 2008), which demonstrates the highest amino acid sequence homology with CFP-T9 among proteins for which crystal structure has been previously reported, for the purpose of obtaining reference data with the intent of forming new disulfide bonds within molecules of CFP-T9 protein. Furthermore, the amino acid sequences of Amadoriase II and CFP-T9 have sequence identity of 34%.

First, the amino acid sequences of CFP-T9 (SEQ ID NO: 1) and Amadoriase II (SEQ ID NO: 15) were aligned using the web-based multiple alignment program, ClustalW (http://www.genomejp/tools/clustalw/) followed by identification of which of the amino acid residues in the amino acid sequence of Amadoriase II corresponds to each of the cysteine residues contained in CFP-T9. As a result, the amino acid residues corresponding to cysteine at position 97, position 200, position 234, position 235, position 280, position 347, position 349 and position 360 of CFP-T9 in the amino acid sequence of Amadoriase II were serine at position 99, valine at position 197, leucine at position 231, arginine at position 232, cysteine at position 278, cysteine at position 335, cysteine at position 337 and aspartic acid at position 348, respectively.

Continuing, a PDB file containing crystal structure data of Amadoriase II (PDB ID: 3DJD) was downloaded from the Protein Data Bank (http://www.pdb.org/pdb/home/home.do), and the crystal structure of Amadoriase II was displayed with PyMOL 0.99rc6 three-dimensional structure display software (Delano Scientific). Continuing, serine at position 99, valine at position 197, leucine at position 231, arginine at position 232 and aspartic acid at position 348 were substituted with cysteine and displayed on PyMOL 0.99rc6 followed by investigating the possibility of each of the cysteine residues at the 8 locations, including cysteine at position 278, cysteine at position 335 and cysteine at position 337, forming intramolecular disulfide bonds. As a result, in the case of substituting serine at position 99 and glycine at position 148 with cysteine, or in the case of substituting aspartic acid at position 348 and leucine at position 358 with cysteine, the possibility was suggested that disulfide bonds are formed between both residues. In addition, glycine at position 148 corresponds to alanine at position 151 in CFP-T9 and leucine at position 358 corresponds to leucine at position 370 in CFP-T9 according to the previously described result of aligning the amino acid sequences of CFP-T9 and Amadoriase II.

Primers composed of SEQ ID NO: 5 and SEQ ID NO: 6 were synthesized with the intent of substituting alanine at position 151 of CFP-T9 with cysteine for the purpose of improving the thermal stability of CFP-T9 due to the formation of new disulfide bonds with reference to the aforementioned data. Next, using recombinant plasmid pKK223-3-CFP-T9 DNA obtained in the manner previously described as template, a PCR reaction was carried out under the same conditions as previously described using the primers of SEQ ID NO: 5 and SEQ ID NO: 6 and KOD-Plus-(Toyobo), followed by carrying out transformation of E. coli strain JM109 and determining the base sequence of DNA encoding amadoriase in plasmid DNA retained by the colonies that grew. As a result, a recombinant plasmid (pKK223-3-CFP-T20) was obtained that encodes modified amadoriase in which alanine at position 151 of the amino acid sequence described in SEQ ID NO: 1 was replaced with cysteine.

(5) Modification of pKK223-3-CFP-T9 DNA Based on Known Enzyme Sequence Data (Modification for Deleting Three Amino Acids on Carboxyl Terminal of PTS1-Like Sequence)

The carboxyl terminal of the amino acid sequence of amadoriase derived from Coniochaeta species is composed of proline at position 435, lysine at position 436 and leucine at position 437. As a result of referring to known data, the possibility was suggested that this sequence is a signal peptide for transporting proteins to peroxisomes in eukaryotic organisms and is equivalent to the motif composed of three amino acids of the carboxyl terminal in the form of PTS1. Since this sequence is also present in CFP-T9, it was also suggested that this region is equivalent to PTS1.

There have been no findings obtained thus far indicating a direct correlation between the loss of the so-called PTS1 sequence and improvement of the thermal stability of the protein produced. On the other hand, if this sequence present in the carboxyl terminal region of amadoriase were to be equivalent to a signal peptide in the form of a PTS1 sequence in amadoriase, it is predicted that that there would be no detrimental effect on amadoriase protein even in the case of having deleted this signal peptide in the expression in an E. coli recombinant, and based on this prediction, an attempt was made to produce a mutant in which this region had been deleted. More specifically, primers composed of the DNA sequences of SEQ ID NO: 7 and SEQ ID NO: 8 were synthesized according to ordinary methods. Next, using the recombinant plasmid pKK223-3-CFP-T9 DNA obtained in the manner previously described as template, a PCR reaction was carried out under the same conditions as previously described using the primers of SEQ ID NO: 7 and SEQ ID NO: 8 and KOD-Plus-(Toyobo), followed by carrying out transformation of E. coli strain JM109 and determining the base sequence of DNA encoding amadoriase in plasmid DNA retained by the colonies that grew. As a result, a recombinant plasmid (pKK223-3-CFP-T21) was obtained that encodes modified amadoriase in which three amino acid residues in the form of proline, lysine and leucine have been deleted from the carboxyl terminal of the amino acid sequence described in SEQ ID NO: 1.

E. coli SHuffle strains were transformed using each of the recombinant plasmids obtained in the manner described above consisting of pKK223-3-CFP-T11, pKK223-3-CFP-T12, pKK223-3-CFP-T13, pKK223-3-CFP-T14, pKK223-3-CFP-T15, pKK223-3-CFP-T16, pKK223-3-CFP-T17, pKK223-3-CFP-T18, pKK223-3-CFP-T19, pKK223-3-CFP-T20 and pKK223-3-CFP-T21.

(6) Production of Various Types of Modified Amadoriase

The resulting E. coli SHuffle strain (pKK223-3-CFP-T11), E. coli SHuffle strain (pKK223-3-CFP-T12), E. coli SHuffle strain (pKK223-3-CFP-T13), E. coli SHuffle strain (pKK223-3-CFP-T14), E. coli SHuffle strain (pKK223-3-CFP-T15), E. coli SHuffle strain (pKK223-3-CFP-T16), E. coli SHuffle strain (pKK223-3-CFP-T17), E. coli SHuffle strain (pKK223-3-CFP-T18), E. coli SHuffle strain (pKK223-3-CFP-T19), E. coli SHuffle strain (pKK223-3-CFP-T20) and E. coli SHuffle strain (pKK223-3-CFP-T21) were cultured for 20 hours at 30° C. in LB-amp medium. Subsequently, each of the cells was washed with pH 8.0 0.01 M phosphate buffer, subjected to ultrasonic crushing and centrifuged for 10 minutes at 15,000 rpm to prepare 1.5 ml of each crude enzyme liquid.

(7) Evaluation of Thermal Stability of Each Type of Modified Amadoriase

The thermal stability of each type of modified amadoriase was evaluated in accordance with the previously described method used to measured thermal stability using each of the crude enzyme liquids prepared in the manner described above as samples. The results are shown in Table 1. In Table 1, CFP-T9 indicates amadoriase derived from E. coli SHuffle strain (pKK223-3-CFP-T9). Furthermore, in the present example, since amadoriase derived from E. coli SHuffle strain (pKK223-3-CFP-T9) in the form of CFP-T9 is used as the enzyme serving as the basis of modification, each of the mutation sites where CFP-T9 has already been introduced are not included in the descriptions for "amino acid mutation" shown in the table.

TABLE 1

| Plasmid | Enzyme | Amino acid mutation | Residual Activity (%) |
|---|---|---|---|
| pKK223-3-CFP-T9 | CFP-T9 | None | 52.6 |
| pKK223-3-CFP-T11 | CFP-T11 | E196D | 62.3 |
| pKK223-3-CFP-T12 | CFP-T12 | S299T | 57.1 |
| pKK223-3-CFP-T13 | CFP-T13 | V323E | 56.3 |
| pKK223-3-CFP-T20 | CFP-T20 | A151C | 87.3 |
| pKK223-3-CFP-T21 | CFP-T21 | Deletion of 3 C-terminal amino acids | 63.2 |

TABLE 2

| Plasmid | Enzyme | Amino acid mutation | Residual Activity (%) |
|---|---|---|---|
| pKK223-3-CFP-T9 | CFP-T9 | None | 52.7 |
| pKK223-3-CFP-T14 | CFP-T14 | F43Y | 64.1 |
| pKK223-3-CFP-T15 | CFP-T15 | H53N | 82.8 |
| pKK223-3-CFP-T16 | CFP-T16 | H53Y | 73.2 |
| pKK223-3-CFP-T17 | CFP-T17 | A185S | 64.0 |
| pKK223-3-CFP-T18 | CFP-T18 | F267Y | 89.1 |
| pKK223-3-CFP-T19 | CFP-T19 | T350A | 55.2 |

As shown in Table 1, under the conditions of the present example, the residual activity of CFP-T9 was 52.6%. In contrast, in 9 mutants selected by random mutation introduction, namely in amadoriase in which glutamic acid at position 196 of CFP-T9 mutated to aspartic acid, serine at position 299 mutated to threonine or valine at position 323 mutated to glutamic acid, residual activity improved to 56% or more in all mutants, and improved to 60% or more in mutants demonstrating remarkably high residual activity. In addition, as shown in Table 2, under the conditions of the present example, the residual activity of CFP-T9 was 52.7%. Although the values for residual activity of CFP-T9 differ between Tables 1 and 2, this is due to different measurement days. Relative to the residual activity of CFP-T9, in 4 mutants selected by random mutation introduction, namely in amadoriase in which phenylalanine at position 43 of CFP-T9 mutated to tyrosine, histidine at position 53 mutated to asparagine, phenylalanine at position 267 mutated to tyrosine or threonine at position 350 mutated to alanine, residual activity improved to 55% or more in all mutants, and improved to 60% or more in mutants demonstrating remarkably high residual activity. Namely, each of these mutation sites was confirmed to be a mutation site that results in an increase in thermal stability of amadoriase. In addition, although heat resistance has also been indicated to improve when tyrosine at position 52 in fructosyl amino acid oxidase derived from Aspergillus nidulans is substituted with histidine, as shown in Table 2, a mutant in which histidine at position 53 of CFP-T9 was substituted with tyrosine also demonstrated improved heat resistance, thus obtaining findings that were the complete opposite of the results for the Aspergillus nidulans-derived fructosyl amino acid oxidase. Aspergillus nidulans-derived fructosyl amino acid oxidase and CFP-T9 have amino acid sequence identity of 74%, and can be presumed to have similar effects with respect to the specific function of the target amadoriase depending on amino acid substitutions at homologous positions. However, this presumption is not valid with respect to position 53 of CFP-T9, resulting in a completely unexpected finding.

In addition, amadoriase in which alanine at position 151 is substituted with cysteine, which is a mutant produced with the intent of improving thermal stability by forming new crosslinks within molecules of amadoriase, demonstrated prominent improvement of residual activity, demonstrating a value in excess of 87%. On the basis of this data, the possibility was suggested that intramolecular crosslinks are actually formed in such mutants, and that thermal stability of amadoriase protein improves significantly as a result thereof.

In this invention, the inventors of the present invention were fortunately able to find novel mutation sites that result in improved thermal stability by taking clues from attempts like those described in the examples. However, it should also be said that the mutation sites tested by the inventors of the present invention could not have been easily conceived from known amadoriase structural data. This is because, despite having referred to data on Amadoriase II, which has the highest level of amino acid sequence homology with CFP-T9 among proteins for which crystal structure has been reported, actual amino acid sequence identity between the two is only 34%. When trying to predict three-dimensional structural data of a known protein having high sequence identity, in the case of only being able to refer to data on a protein having a low level of identity in this manner, it is commonly understood by a person with ordinary skill in the art that the prediction of three-dimensional structure or amino acids located near active sites is unlikely to be successful. Namely, it would be uncommon for a person with ordinary skill in the art to predict that proteins having a low degree of sequence identity to this extent would have similar functions. This is because, realistically, it is commonly known that it would be extremely difficult to say that various types of known proteins are the same enzyme by taking a hint from a search of sequence identity to this degree.

In actuality, there were also assumed to be candidates for mutation sites other than position 151 in the predictions described in the examples. For example, a method consisting of forming an intramolecular crosslink with cysteine at position 360 by substituting leucine at position 370 with cysteine was also expected to be promising to a certain extent in terms of prediction. However, even when this type of mutation was actually introduced, the thermal stability of the resulting modified amadoriase did not improve, and conversely tended to decrease slightly. This finding also supports the fact that predicting an effective mutation site as in the present invention is not always easy based on information on known enzymes having low sequence identity.

Moreover, in the case of mutants produced by deleting three amino acids of the carboxyl terminal as well, which have the possibility of being equivalent to a so-called PTS1 sequence, residual activity (%) exceeded 60% and remarkable improvement was observed.

Until now, there had been no findings whatsoever indicating that the thermal stability of a produced protein can be improved by deleting a region equivalent to the so-called PTS1 region. Thus, the result obtained here is a remarkable result that was unable to be predicted even by the inventors of the present invention, and is quite surprising. Although it is currently not certain whether or not several amino acids of the carboxyl terminal of amadoriase protein actually constitute a region that can be equivalent to a so-called PTS1 sequence, and the specific mechanism of action by which the deletion of this region results in improved thermal stability is still unclear at the present time, in actuality, as can be understood from the plurality of amadoriases shown in Table 1, even though the amino acids may not be the same, in the case of adopting the viewpoint that these amadoriases have a sequence of amino acid residues capable of being equivalent to a so-called PTS1 sequence motif, the possibility is suggested that a sequence capable of being equivalent to a similar signal sequence is deleted by deletion of three amino acids of the carboxyl terminal in a plurality of amadoriases, and that as a result thereof, effective thermal stability is able to be imparted to various types of amadoriase.

These mutation sites of the present invention are not only effective as independent mutations, but are also expected to contribute to the creation of mutants having practical advantages as a result of combining with various types of known mutants already known or by combining mutations of the present invention.

Example 2

(Accumulation of Heat Resistance-Improving Mutations)

Mutations resulting in improved heat resistance were attempted to be accumulated by producing multiple mutants (double mutants, triple mutants and quadruple mutants) for the purpose of acquiring amadoriase having even more enhanced thermal stability as a result of accumulating mutations by combining the 11 thermal stability-improving mutations found in Example 1 based on those findings.

More specifically, using the various recombinant plasmid DNA shown in Table 3 as templates, PCR reactions were carried out under the same conditions as Example 1 using combinations of each of the synthetic oligonucleotides shown in Table 3 as primers followed by transforming E. coli strain JM109 and determining the base sequence of DNA encoding amadoriase present in plasmid DNA retained by the colonies that grew. As a result, a double mutant in the form of pKK223-3-CFP-T22, in which alanine at position 151 was substituted with cysteine and serine at position 299 was substituted with threonine, a triple mutant in the form of pKK223-3-CFP-T23, in which alanine at position 151 was substituted with cysteine, glutamic acid at position 196 was substituted with aspartic acid and serine at position 299 was substituted with threonine, a triple mutant in the form of pKK223-3-CFP-T24, in which alanine at position 151 was substituted with cysteine, serine at position 299 was substituted with threonine and three amino acid residues were deleted from the carboxyl terminal, a quadruple mutant in the form of pKK223-3-CFP-T25, in which alanine at position 151 was substituted with cysteine, glutamic acid at position 196 was substituted with aspartic acid, serine at position 299 was substituted with threonine and valine at position 323 was substituted with glutamic acid, and a quadruple mutant in the form of pKK223-3-CFP-T26, in which alanine at position 151 was substituted with cysteine, glutamic acid at position 196 was substituted for aspartic acid, serine at position 299 was substituted with threonine, and three amino acid residues were deleted from the carboxyl terminal, were obtained.

E. coli SHuffle strain was transformed under the same conditions as previously described to obtain E. coli SHuffle strain (pKK223-3-CFP-T22), E. coli SHuffle strain (pKK223-3-CFP-T23), E. coli SHuffle strain (pKK223-3-CFP-T24), E. coli SHuffle strain (pKK223-3-CFP-T25) and E. coli SHuffle strain (pKK223-3-CFP-T26).

Moreover, using the various recombinant plasmid DNA shown in Table 4 as templates, PCR reactions were carried out under the same conditions as Example 1 using combinations of each of the synthetic oligonucleotides shown in Table 4 as primers followed by transforming E. coli strain JM109 and determining the base sequence of DNA encoding amadoriase present in plasmid DNA retained by the colonies that grew. As a result, a double mutant in the form of pKK223-3-CFP-T27, in which phenylalanine at position 43 was substituted with tyrosine and alanine at position 151 was substituted with cysteine, a double mutant in the form of pKK223-3-CFP-T28, in which phenylalanine at position 43 was substituted with tyrosine and three amino acid residues were deleted from the carboxyl terminal, a triple mutant in the form of pKK223-3-CFP-T29, in which phenylalanine at position 43 was substituted with tyrosine, threonine at position 350 was substituted with alanine and three amino acid residues were deleted from the carboxyl terminal, a triple mutant in the form of pKK223-3-CFP-T30, in which phenylalanine at position 43 was substituted with tyrosine, alanine at position 151 was substituted with cysteine and threonine at position 350 was substituted with alanine, a triple mutant in the form of pKK223-3-CFP-T31, in which phenylalanine at position 43 was substituted with tyrosine, alanine at position 151 was substituted with cysteine and three amino acid residues were deleted from the carboxyl terminal, and a quadruple mutant in the form of pKK223-3-CFP-T32, in which phenylalanine at position 43 was substituted with tyrosine, alanine at position 151 was substituted with cysteine, threonine at position 350 was substituted with alanine and three amino acid residues were deleted from the carboxyl terminal, were obtained.

E. coli SHuffle strain was transformed under the same conditions as previously described to obtain E. coli SHuffle strain (pKK223-3-CFP-T27), E. coli Shuffle strain (pKK223-3-CFP-T28), E. coli SHuffle strain (pKK223-3-CFP-T29), E. coli SHuffle strain (pKK223-3-CFP-T30), E. coli SHuffle strain (pKK223-3-CFP-T31) and E. coli SHuffle strain (pKK223-3-CFP-T32).

The E. coli SHuffle strain (pKK223-3-CFP-T22), E. coli SHuffle strain (pKK223-3-CFP-T23), E. coli Shuffle strain (pKK223-3-CFP-T24), E. coli SHuffle strain (pKK223-3-CFP-T25), E. coli SHuffle strain (pKK223-3-CFP-T26), E. coli SHuffle strain (pKK223-3-CFP-T27), E. coli SHuffle strain (pKK223-3-CFP-T28), E. coli SHuffle strain (pKK223-3-CFP-T29), E. coli SHuffle strain (pKK223-3-CFP-T30), E. coli Shuffle strain (pKK223-3-CFP-T31) and E. coli SHuffle strain (pKK223-3-CFP-T32), having the ability to produce the modified amadoriase obtained in the manner previously described, were cultured according to the previously described method to prepare 1.5 ml of crude enzyme liquids of each type of modified amadoriase. The thermal stability of each type of modified amadoriase was evaluated using each of the resulting crude enzyme liquids as samples in accordance with the method used to measured thermal stability in compliance with Example 1 with the exception of changing heating conditions to more severe conditions consisting of heating for 30 minutes at 60° C. The results are shown in Tables 3 and 4.

TABLE 3

| Plasmid | Template plasmid | Enzyme | Amino acid mutation | SEQ ID NO of Oligonucleotides Used | Residual Activity (%) |
| --- | --- | --- | --- | --- | --- |
| pKK223-3-CFP-T9 | None | CFP-T9 | None | None | 0.34 |
| pKK223-3-CFP-T20 | None | CFP-T20 | A151C | 5, 6 | 26.0 |
| PKK223-3-CFP-T22 | pKK223-3-CFP-T12 | CFP-T22 | A151C/S299T | 5, 6 | 33.6 |
| pKK223-3-CFP-T23 | pKK223-3-CFP-T22 | CFP-T23 | A151C/E196D/S299T | 9, 10 | 36.1 |
| pKK223-3-CFP-T24 | pKK223-3-CFP-T22 | CFP-T24 | A151C/S299T/Deletion of 3 C-terminal amino acids | 7, 8 | 40.8 |
| pKK223-3-CFP-T25 | pKK223-3-CFP-T23 | CFP-T25 | A151C/E196D/S299T/V323E | 11, 12 | 42.1 |
| pKK223-3-CFP-T26 | pKK223-3-CFP-T23 | CFP-T26 | A151C/E196D/S299T/Deletion of 3 C-terminal amino acids | 7, 8 | 54.1 |

TABLE 4

| Plasmid | Template plasmid | Enzyme | Amino acid mutation | SEQ ID NO of Oligonucleotides Used | Residual Activity (%) |
| --- | --- | --- | --- | --- | --- |
| pKK223-3-CFP-T9 | None | CFP-T9 | None | None | 0.36 |
| pKK223-3-CFP-T27 | pKK223-3-CFP-T14 | CFP-T27 | F43Y/A151C | 5, 6 | 70.2 |
| pKK223-3-CFP-T28 | pKK223-3-CFP-T14 | CFP-T28 | F43Y/Deletion of 3 C-terminal amino acids | 7, 8 | 2.5 |
| pKK223-3-CFP-T29 | pKK223-3-CFP-T28 | CFP-T29 | F43Y/T350A/Deletion of 3 C-terminal amino acids | 13, 14 | 4.8 |

TABLE 4-continued

| Plasmid | Template plasmid | Enzyme | Amino acid mutation | SEQ ID NO of Oligonucleotides Used | Residual Activity (%) |
|---|---|---|---|---|---|
| pKK223-3-CFP-T30 | pKK223-3-CFP-T27 | CFP-T30 | F43Y/A151C/T350A | 13, 14 | 71.7 |
| pKK223-3-CFP-T31 | pKK223-3-CFP-T28 | CFP-T31 | F43Y/A151C/Deletion of 3 C-terminal amino acids | 5, 6 | 78.3 |
| pKK223-3-CFP-T32 | pKK223-3-CFP-T30 | CFP-T32 | F43Y/A151C/T350A/Deletion of 3 C-terminal amino acids | 7, 8 | 81.3 |

As shown in Tables 3 and 4, under the conditions of the present example, the remaining activities of CFP-T9 were 0.34% and 0.36%, thereby confirming that even CFP-T9, which is thought to have the most superior thermal stability among conventional amadoriases under such severe temperature conditions, ends up, losing nearly all of its activity.

In contrast, residual activity improved remarkably in all of the various types of multiple mutants produced by combining various types of independent mutations confirmed in Example 1. More specifically, the residual activity of the double mutant in which phenylalanine at position 43 was substituted with alanine and three amino acid residues were deleted from the carboxyl terminal was 2.5% and improved in comparison with CFP-T9. Moreover, the residual activity of the triple mutant in which threonine at position 350 was substituted with alanine in this mutation was 4.8% and further improved in comparison with CFP-T9. In addition, the residual activity of a mutant in which alanine at position 151 was substituted with cysteine was 26% and remarkably improved in comparison with CFP-T9. Moreover, double mutants, triple mutants and quadruple mutants obtained by accumulating mutations by sequentially adding other mutations to this mutation also demonstrated remarkably improved residual activity in comparison with CFP-T9, and these multiple mutants were confirmed to be mutation sites that further improve the thermal stability of amadoriase having improved thermal stability.

Moreover, each time a mutation was accumulated in the mutant in which alanine at position 151 was substituted with cysteine or the double mutant in which phenylalanine at position 43 was substituted with alanine and three amino acid residues were deleted from the carboxyl terminal, the thermal stability of the resulting multiple mutant increased incrementally, and amadoriase having even more superior thermal stability was clearly determined to able to be produced by suitably combining the mutation sites of the present invention confirmed in Example 1.

Example 3

(Introduction of Mutation Site in Amadoriase Gene Derived from *Eupenicillium terrenum*)

SEQ ID NO: 16 is an amino acid sequence of *Eupenicillium terrenum*-derived amadoriase introduced with mutations that improve thermal stability (G184D, N272D, H388Y), and the activity of *Eupenicillium terrenum*-derived amadoriase has been confirmed by expressing recombinant plasmid pUTE100K'-EFP-T5 inserted with a gene (SEQ ID NO: 17) encoding the amino acid sequence of SEQ ID NO: 16 in *E. coli* (see Patent Document 16).

In order to introduce a heat resistance-improving mutation into *Eupenicillium terrenum*-derived amadoriase, recombinant plasmid pUTE100K'-EFP-T5 was used as template and a PCR reaction was carried out under the same conditions as Example 1 using the synthetic oligonucleotides of SEQ ID NO: 18 and SEQ ID NO: 19 followed by transforming *E. coli* strain JM109 and determining the base sequence of DNA encoding amadoriase in plasmid DNA retained by the colonies that grew. As a result, a recombinant plasmid encoding *Eupenicillium terrenum*-derived amadoriase gene in which glycine at position 151 of the amino acid sequence described in SEQ ID NO: 16 was substituted with cysteine was obtained (pUTE100K'-EFP-T5-G151C).

*E. coli* SHuffle strain was transformed under the same conditions as Example 1 to obtain *E. coli* SHuffle strain (pUTE100K'-EFP-T5-G151C).

Example 4

(Evaluation of Effect of Improving Heat Resistance of *Eupenicillium terrenum*-Derived Amadoriase Introduced with Point Mutation)

*E. coli* SHuffle strain (pUTE100K'-EFP-T5-G151C) having the ability to produce the modified amadoriase obtained in the manner described above was cultured using the method of Example 1 to prepare 1.5 ml of crude enzyme liquids of each type of modified amadoriase. The thermal stability of each type of modified amadoriase was evaluated using each of the resulting crude enzyme liquids as samples in accordance with the method used to measured thermal stability in compliance with Example 1. The results are shown in Table 5.

TABLE 5

| Plasmid | Enzyme | Amino acid mutation | Residual Activity (%) |
|---|---|---|---|
| pKK223-3-EFP-T5 | EFP-T5 | None | 0.77 |
| pKK223-3-EFP-T5-G151C | EFP-T5-G151C | G151C | 51.2 |

As shown in Table 5, under the conditions of the present example, the residual activity of EFP-T5 was 0.77%. In contrast, the residual activity of amadoriase in which glycine at position 151 was substituted with cysteine was 51.2% and improved remarkably in comparison with EFP-T5. Accordingly, substitution of an amino acid at the position corresponding to alanine at position 151 of amadoriase derived from *Coniochaeta* species indicated in SEQ ID NO: 1 with cysteine was determined to be an effective substitution for the production of amadoriase having improved heat resistance in the case of *Eupenicillium terrenum*-derived amadoriase as well.

Example 5

(Expression of *Phaeosphaeria nodorum*-Derived Fructosyl Peptide Oxidase in *E. coli*)

Fructosyl peptide oxidase derived from *Phaeosphaeria nodorum* was attempted to be expressed in *E. coli*. The previously determined amino acid sequence of *Phaeosphaeria nodorum*-derived fructosyl peptide oxidase is shown in SEQ ID NO: 20 (see, for example, Biotechnology and Bioengineering, 106, 358-366, 2010). A 1314 bp gene indicated in SEQ ID NO: 21 (containing stop codon TAA), which encodes 437 amino acids indicated in this SEQ ID NO: 20 and contains a codon optimized for expression in *E. coli*, was acquired by total synthesis of cDNA by carrying out PCR on the gene fragment in accordance with an established method. At this time, an EcoRI site and HindIII site were respectively added to the 5'-terminal and 3'-terminal of SEQ ID NO: 21. In addition, the full length of an amino acid sequence predicted from a cloned gene sequence was confirmed to match the sequence of *Phaeosphaeria nodorum*-derived fructosyl peptide oxidase of FIG. 1.

Continuing, the following procedure was carried out in order to express the acquired gene of SEQ ID NO: 21 in *E. coli*. First, the aforementioned totally synthesized gene was treated with two types of restrictases consisting of EcoRI and HindIII (Takara Bio) followed by inserting into the EcoRI-HindIII site of pKK223-3-Vector (Amersham Biotech) to acquire recombinant plasmid pKK223-3-PnFX, followed by transforming *E. coli* SHuffle strain under the same conditions as Example 1 to obtain *E. coli* SHuffle strain (pKK223-3-PnFX).

The *E. coli* SHuffle strain (pKK223-3-PnFX) having the ability to produce the *Phaeosphaeria nodorum*-derived fructosyl peptide oxidase obtained in the manner described above was cultured using the method of Example 1 to prepare 1.5 ml of crude enzyme liquids. Each of the resulting crude enzyme liquids was then used as a sample to confirm the presence of *Phaeosphaeria nodorum*-derived fructosyl peptide oxidase activity in accordance with the method used to measured thermal stability in compliance with Example 1.

Example 6

(Introduction of Point Mutation in *Phaeosphaeria nodorum*-Derived Fructosyl Peptide Oxidase)

In order to introduce a heat resistance-improving mutation into *Phaeosphaeria nodorum*-derived fructosyl peptide oxidase, recombinant plasmid pKK223-3-PnFX was used as template and a PCR reaction was carried out under the same conditions as Example 1 using the synthetic oligonucleotides of SEQ ID NO: 22 and SEQ ID NO: 23 and KOD-Plus-(Toyobo) followed by transforming *E. coli* strain JM109 and determining the base sequence of DNA encoding amadoriase in plasmid DNA retained by the colonies that grew. As a result, a recombinant plasmid encoding *Phaeosphaeria nodorum*-derived fructosyl peptide oxidase gene, in which alanine at position 149 of the amino acid sequence described in SEQ ID NO: 20 was substituted with cysteine, was obtained (pKK223-3-PnFX-A149C).

*E. coli* Shuffle strain was transformed under the same conditions as previously described to obtain *E. coli* Shuffle strain (pKK223-3-PnFX-A149C).

Continuing, In order to introduce a heat resistance-improving mutation into *Phaeosphaeria nodorum*-derived fructosyl peptide oxidase, recombinant plasmid pKK223-3-PnFX was used as template and a PCR reaction was carried out under the same conditions as Example 1 using the synthetic oligonucleotides of SEQ ID NO: 24 and SEQ ID NO: 25 and KOD-Plus-(Toyobo) followed by transforming *E. coli* strain JM109 and determining the base sequence of DNA encoding amadoriase in plasmid DNA retained by the colonies that grew. As a result, a recombinant plasmid encoding modified fructosyl peptide oxidase gene, in which three amino acid residues in the form of alanine, asparagine and leucine were deleted from the carboxyl terminal of the amino acid sequence described in SEQ ID NO: 20, was obtained (pKK223-3-PnFX-ΔPTS1).

*E. coli* Shuffle strain was transformed under the same conditions as previously described to obtain *E. coli* Shuffle strain (pKK223-3-PnFX-ΔPTS1).

Example 7

(Evaluation of Effect of Improving Heat Resistance of *Phaeosphaeria nodorum*-Derived Fructosyl Peptide Oxidase Introduced with Point Mutation)

*E. coli* Shuffle strain (pKK223-3-PnFX-A149C) and *E. coli* Shuffle strain (pKK223-3-PnFX-ΔPTS1) having the ability to produce the modified fructosyl peptide oxidase obtained in the manner described above were cultured using the method of Example 1 to prepare 1.5 ml of crude enzyme liquids of each type of modified fructosyl peptide oxidase. The thermal stability of each type of modified fructosyl peptide oxidase was evaluated using each of the resulting crude enzyme liquids as samples in accordance with the method used to measured thermal stability in compliance with Example 1. The results are shown in Table 6.

TABLE 6

| Plasmid | Enzyme | Amino acid mutation | Residual Activity (%) |
|---|---|---|---|
| pKK223-3-PnFX | PnFX | None | 25.0 |
| pKK223-3-PnFX-A149C | PnFX-A149C | A149C | 46.2 |
| pKK223-3-PnFX-ΔPTS1 | PnFX-ΔPTS1 | Deletion of 3 C-terminal amino acids | 37.5 |

As shown in Table 6, under the conditions of the present example, the residual activity of PnFX was 25.0%. In contrast, the residual activity of fructosyl peptide oxidase in which alanine at position 149 was substituted with cysteine was 46.2%, the residual activity of fructosyl peptide oxidase in which three amino acid residues were deleted from the carboxyl terminal was 37.5%, and residual activity improved remarkably in comparison with PnFX. Accordingly, substitution of an amino acid at the position corresponding to alanine at position 151 of amadoriase derived from *Coniochaeta* species indicated in SEQ ID NO: 1 with cysteine and deletion of three amino acid residues from the carboxyl terminal were determined to be an effective substitution and deletion for the production of fructosyl peptide oxidase having improved heat resistance in the case of *Phaeosphaeria nodorum*-derived fructosyl peptide oxidase as well.

The invention claimed is:

1. A modified amadoriase comprising an amino acid sequence having an identity of 90% or more with SEQ ID NO: 1, and comprising a modification as follows:
   (a) has three amino acid residues deleted from the carboxyl terminal, or has an amino acid substitution as set forth in any of the following (b) to (j):
   (b) the amino acid at the position corresponding to alanine at position 151 is substituted with another amino acid,
   (c) the amino acid at the position corresponding to phenylalanine at position 43 is substituted with another amino acid,
   (d) the amino acid at the position corresponding to histidine at position 53 is substituted with another amino acid,
   (e) the amino acid at the position corresponding to phenylalanine at position 267 is substituted with another amino acid,
   (f) the amino acid at the position corresponding to threonine at position 350 is substituted with another amino acid,
   (g) the amino acid at the position corresponding to alanine at position 185 is substituted with another amino acid,
   (h) the amino acid at the position corresponding to glutamic acid at position 196 is substituted with another amino acid,
   (i) the amino acid at the position corresponding to serine at position 299 is substituted with another amino acid, or
   (j) the amino acid at the position corresponding to valine at position 323 is substituted with another amino acid; wherein residual activity (%) following a heat treatment at 55° C. for 30 minutes at pH 7.0 is improved in comparison with amadoriase having an amino acid sequence of SEQ ID NO: 1 or an amino acid sequence having an identity of 90% or more with SEQ ID NO: 1 prior to being modified.

2. A modified amadoriase comprising an amino acid sequence
having an identity of 90% or more with SEQ ID NO: 1, and comprising a modification as follows:
(k) has three amino acid residues deleted from the carboxyl terminal, or has with an amino acid substitution as set forth in any of the following (l) to (t):
(l) the amino acid at the position corresponding to alanine at position 151 is substituted with cysteine,
(m) the amino acid at the position corresponding to phenylalanine at position 43 is substituted with tyrosine,
(n) the amino acid at the position corresponding to histidine at position 53 is substituted with asparagine or tyrosine,
(o) the amino acid at the position corresponding to phenylalanine at position 267 is substituted with tyrosine,
(p) the amino acid at the position corresponding to threonine at position 350 is substituted with alanine,
(q) the amino acid at the position corresponding to alanine at position 185 is substituted with serine,
(r) the amino acid at the position corresponding to glutamic acid at position 196 is substituted with aspartic acid,
(s) the amino acid at the position corresponding to serine at position 299 is substituted with threonine, or
(t) the amino acid at the position corresponding to valine at position 323 is substituted with glutamic acid;
wherein residual activity following a heat treatment at 55° C. for 30 minutes at pH 7.0 is improved in comparison with amadoriase having an amino acid sequence of SEQ ID NO:1 or an amino acid sequence having an identity of 90% or more with SEQ ID NO: 1 prior to being modified.

3. A modified amadoriase comprising an amino acid sequence having an identity of 90% or more with SEQ ID NO: 1, and comprising a modification selected from the group consisting of the following (u) to (ae):
(u) substitution of the amino acid at the position corresponding to alanine at position 151 with cysteine and substitution of the amino acid at the position corresponding to serine at position 299 with threonine,
(v) substitution of the amino acid at the position corresponding to phenylalanine at position 43 with tyrosine and substitution of the amino acid at the position corresponding to alanine at position 151 with cysteine,
(w) substitution of the amino acid at the position corresponding to phenylalanine at position 43 with tyrosine and deletion of the amino acid residues at the positions corresponding to the three amino acid residues from the carboxyl terminal,
(x) substitution of the amino acid at the position corresponding to alanine at position 151 with cysteine, substitution of the amino acid at the position corresponding to glutamic acid at position 196 with aspartic acid, and substitution of the amino acid at the position corresponding to serine at position 299 with threonine,
(y) substitution of the amino acid at the position corresponding to alanine at position 151 with cysteine, substitution of the amino acid at the position corresponding to serine at position 299 with threonine, and deletion of the amino acid residues at the positions corresponding to the three amino acid residues from the carboxyl terminal,
(z) substitution of the amino acid at the position corresponding to phenylalanine at position 43 with tyrosine, substitution of the amino acid at the position corresponding to threonine at position 350 with alanine, and deletion of the amino acid residues at the positions corresponding to the three amino acid residues from the carboxyl terminal,
(aa) substitution of the amino acid at the position corresponding to phenylalanine at position 43 with tyrosine, substitution of the amino acid at the position corresponding to alanine at position 151 with cysteine, and deletion of the amino acid residues at the positions corresponding to the three amino acid residues from the carboxyl terminal,
(ab) substitution of the amino acid at the position corresponding to phenylalanine at position 43 with tyrosine, substitution of the amino acid at the position corresponding to alanine at position 151 with cysteine, and substitution of the amino acid at the position corresponding to threonine at position 350 with alanine,
(ac) substitution of the amino acid at the position corresponding to alanine at position 151 with cysteine, substitution of the amino acid at the position corresponding to glutamic acid at position 196 with aspartic acid, substitution of the amino acid at the position corresponding to serine at position 299 with threonine, and substitution of the amino acid at the position corresponding to valine at position 323 with glutamic acid,
(ad) substitution of the amino acid at the position corresponding to alanine at position 151 with cysteine, substitution of the amino acid at the position corresponding to glutamic acid at position 196 with aspartic acid, substitution of the amino acid at the position corresponding to serine at position 299 with threonine, and deletion of the amino acid residues at the positions corresponding to the three amino acid residues from the carboxyl terminal, and
(ae) substitution of the amino acid at the position corresponding to phenylalanine at position 43 with tyrosine, substitution of the amino acid at the position corresponding to alanine at position 151 with cysteine, substitution of the amino acid at the position corresponding to threonine at position 350 with alanine, and deletion of the amino acid residues at the positions corresponding to the three amino acid residues from the carboxyl terminal,
wherein residual activity following a heat treatment at 60° C. for 30 minutes at pH 7.0 is improved in comparison with amadoriase having an amino acid sequence of SEQ ID NO: 1 or an amino acid sequence having an identity of 90% or more with SEQ ID NO: 1 prior to the modification.

4. A kit for measuring a glycated protein, containing the amadoriase according to claim 1 and a protease.

5. A kit for measuring glycated hemoglobin, containing the amadoriase according to claim 1 and a protease.

6. A kit for measuring a glycated protein or glycated hemoglobin containing the amadoriase according to claim 2 and a protease.

7. A kit for measuring a glycated protein or glycated hemoglobin containing the amadoriase according to claim 3 and a protease.

8. The kit according to claim 6 further containing a peroxidase.

9. The kit according to claim 6 further containing a peroxidase.

* * * * *